United States Patent
Lang et al.

(10) Patent No.: US 11,963,789 B2
(45) Date of Patent: Apr. 23, 2024

(54) MEASURING AND/OR CHARACTERIZING FEEDING BEHAVIOR

(71) Applicants: Scott Buckley, Portland, OR (US); Neil R. M. Buist, Portland, OR (US); W. Christopher Lang, New Albany, IN (US)

(72) Inventors: W. Christopher Lang, New Albany, IN (US); Scott Buckley, Portland, OR (US); Neil Buist, Portland, OR (US)

(73) Assignee: THE TRUSTEES OF INDIANA UNIVERSITY, Bloomington, IN (US)

(*) Notice: Subject to any disclaimer, the term of this patent is extended or adjusted under 35 U.S.C. 154(b) by 0 days.

(21) Appl. No.: 15/933,356

(22) Filed: Mar. 22, 2018

(65) Prior Publication Data

US 2023/0022316 A1    Jan. 26, 2023

Related U.S. Application Data

(60) Provisional application No. 62/475,137, filed on Mar. 22, 2017.

(51) Int. Cl.
A61B 5/00 (2006.01)

(52) U.S. Cl.
CPC .......... *A61B 5/4542* (2013.01); *A61B 5/7242* (2013.01); *A61B 5/7246* (2013.01); *A61B 5/7257* (2013.01); *A61B 5/7267* (2013.01); *A61B 5/7282* (2013.01); *A61B 2503/045* (2013.01); *A61B 2562/0247* (2013.01)

(58) Field of Classification Search
CPC ... A61B 5/4542; A61B 5/7242; A61B 5/7246; A61B 5/7257; A61B 5/7267; A61B 5/7282; A61B 2503/045; A61B 2562/0247

USPC ........................................................ 600/590
See application file for complete search history.

(56) References Cited

U.S. PATENT DOCUMENTS

| | | | |
|---|---|---|---|
| 6,033,367 A | 3/2000 | Goldfield | |
| 6,109,100 A | 8/2000 | Buckley | |
| 8,413,502 B2 | 4/2013 | Zemel | |
| 8,473,219 B2 | 6/2013 | Kaplan | |
| 9,974,476 B2* | 5/2018 | Aron | A61B 5/682 |
| 2006/0074354 A1* | 4/2006 | Barlow | A61B 5/486 |
| | | | 600/590 |
| 2008/0077183 A1* | 3/2008 | Cohen | A61B 5/038 |
| | | | 606/234 |
| 2010/0131454 A1* | 5/2010 | Kaplan | A23L 33/40 |
| | | | 706/54 |

(Continued)

FOREIGN PATENT DOCUMENTS

| | | |
|---|---|---|
| WO | 2009132334 A1 | 10/2009 |
| WO | 2014015180 A1 | 1/2014 |

OTHER PUBLICATIONS

Lang, William Christopher, et al. "Quantification of Intraoral Pressures During Nutritive Sucking: Methods with Normal Infants" Sep. 19, 2010, Dysphagia, 26:277-286 (Year: 2010).*

(Continued)

*Primary Examiner* — May A Abouelela
*Assistant Examiner* — Anna Roberts
(74) *Attorney, Agent, or Firm* — Womble Bond Dickinson (US) LLP

(57) ABSTRACT

A feeding analysis system reviews collected feeding data and provides analysis of data regarding nutritive sucking, feeding, and related activity.

55 Claims, 16 Drawing Sheets

(56) References Cited

U.S. PATENT DOCUMENTS

| | | | | |
|---|---|---|---|---|
| 2014/0228714 A1* | 8/2014 | Chau | .................... | A61B 5/7267 600/593 |
| 2015/0196247 A1* | 7/2015 | Lau | ......................... | G01F 1/363 600/301 |
| 2020/0129380 A1* | 4/2020 | Sazonov | .............. | A61B 5/4205 |

OTHER PUBLICATIONS

Neil R.M. Buist, et al., "Electronic Quantitation of Sucking in Infants," May 5, 2003, 1 page.

Caitlin F. Fitzgerald, "Variation in Intra-Bottle Pressure Generated by Infants With Normal Palate, Infants With Cleft Palate, and Infants With Velopharyngeal Insufficiency During Nutritive Sucking," thesis, Portland State University, 2007, 80 pages.

R. Valeryn, et al., "Quantitation of Intraoral Pressures During Nutritive Sucking in Preterm Infant" Abstract 6, (2009), 1 page.

W.C. Lang, A.J. Jones, et al. "Quantitation of Intraoral Pressures during Nutritive Feeding. 1. Normal Infants," APS/SPR meeting Baltimore (May 2009), 1 page.

N.R.M. Buist, et al., "Quantification of Nutritive Sucking: A New Approach to Developmental Assessment?," ICEM Abstract (May 27, 2009), 1 page.

N. Buist, "Quantification of Nutritive Sucking Behavior in Infants," 11th Annual NIH SBIR/STTR Conference Poster Session Abstract Submission Form, (2009), 5 pages.

A. Scherman, et al., "Age-Related Quantitation of Sucking Behavior in Normal Infants," Abstract, Pediatric Academic Society Annual Meeting, San Diego, CA (2015), 1 page.

A. Scherman, et al., "Age-Related Quantitation of Sucking Behavior in Normal Infants," Poster Pediatric Academic Society Annual Meeting, San Diego, CA (2015), 1 page.

A. Scherman, et al., "Quantification of Nutritive Sucking Among Preterm and Full-Term Infants," Research and Reports in Neonatology, 2018:8, pp. 53-63 (2018), 11 pages.

W.C. Lang, et al. "Quantification of Intraoral Pressures During Nutritive Sucking: Methods with Normal Infants," Dysphagia 26:277-286, (2011) (Published Online Sep. 19, 2010), 10 pages.

Momin, Shabnam R. et al., "Rationale and design of the Baylor Infant Twin Study—A study assessing obesity-related risk factors from infancy," Obesity Science and Practice, vol. 7, pp. 63-70 (Oct. 4, 2020), 8 pages.

Da Costa, SP et al., "Sucking and swallowing in infants and diagnostic tools," Journal of Perinatology, vol. 28, pp. 247-257 (Jan. 17, 2008), 11 pages.

\* cited by examiner

Scatterplot Produced by Decision Tree Algorithm Distinguishing Between Normal and Nonnormal Suck Patterns from Very Small Dataset.

Scatterplot Produced by KNN Algorithm Distinguishing Between Normal and Nonnormal Suck Patterns from Very Small Dataset.

MEASURING AND/OR CHARACTERIZING FEEDING BEHAVIOR

CROSS REFERENCE TO RELATED APPLICATIONS

This application claims priority from U.S. Provisional Patent Application 62/475,137, filed Mar. 22, 2017.

STATEMENT REGARDING FEDERALLY SPONSORED RESEARCH OR DEVELOPMENT

This invention was made with Government support under Grant No. 2 R44 HD038234-02, Grant No. 5 R44 HD038234-03, and Grant No. 2R44HD038234-04, awarded by the National Institutes of Health. The Government has certain rights in the invention.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

Specific embodiments involve monitoring, measurement, and documentation of feeding (nutritive ingestion of fluids) by a human or animal subject. Embodiments are directed to the monitoring, measurement and documentation of sucking force applied by the subject for use in gauging the subject's strength, growth, developmental status, coordination or general health. Additional embodiments involve analyzing biophysical diagnostic data produced by a feeding detector (e.g., a fluid container such as a baby feeding-bottle fitted with one or more pressure sensor(s) or other sensing devices) to characterize infant or other feeding behavior. Nutritive sucks and suck bursts are determined according to specific embodiments. Measures of consistency and strength of feeding based on measurement of sucks and suck bursts are detailed, as are proxy measures based on Fourier transforms that do not rely upon suck or burst identification.

BACKGROUND

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

SUMMARY

This description introduces a selection of concepts that are further described or can be further understood from other papers submitted with this application or incorporated by reference. Key features or essential features of the claimed subject matter are discussed throughout this submission including in the appendix, thus no individual part of this submission is intended to determine the scope of the claimed subject matter.

As an example of one type of system that can generate data for use according to specific embodiments or into which embodiments may be incorporated, a feeding monitor system as described herein generally provides one or more of data acquisition, monitoring, storage, display, printing, analysis, and programmable gated flow which is responsive to feeding or fluid flow to a human or animal subject sucking on a nipple or other outlet connected to a supply of feeding fluid stored in a reservoir. According to specific embodiments, one or more chambers positioned between the reservoir and the outlet include one or more pressure sensors and optionally a volumetric sensor or fluid flow meter that provide output signals indicating suck-force pressure and/or volumetric and/or fluid flow behavior. An optional processor-controlled valve provides gated availability of the feeding fluid so it is dispensed on demand, according to an optionally programmable or configurable set of criteria. The output signals can be displayed, analyzed, or stored in a wide variety of forms or formats, and may be viewed, stored or used to measure and/or analyze feeding performance and feeding patterns. In further embodiments, an optional solid nipple with a narrow feeding passage prevents or reduces monitoring errors due to gas compression, gas expansion, bubble formation, or other factors. According to specific embodiments, other feeding monitoring systems may be used to generate initial data to be analyzed, as discussed herein.

Systems, methods, and apparatuses according to specific embodiments have wide application, including without limitation use in a neonatal intensive care environment, general care baby centers, hospitals, medical offices, outpatient clinics, etc. for evaluation of feeding, display of feeding patterns, diagnosis or screening of disease or disability, gauging strength of oropharyngeal function, and evaluating response to therapy for feeding difficulties of patients.

BRIEF DESCRIPTION OF THE DRAWINGS

FIG. 8A is intended as an operational diagram and does not show relative dimensions or exact placement of parts.)

DETAILED DESCRIPTION OF SPECIFIC EMBODIMENTS

Glossary

Figure 1A:
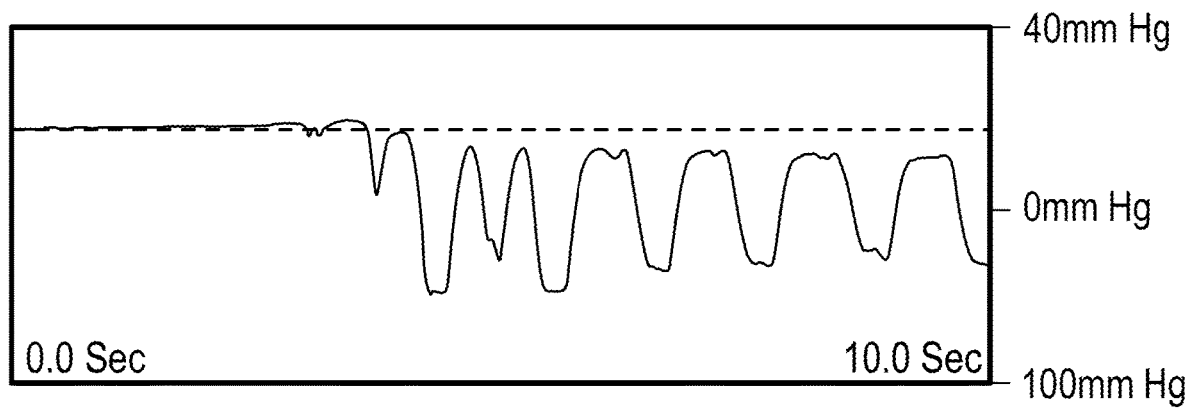
FIG. 1A-D are graphs illustrating captured data and data analysis for automatic suck identification or feature identification according to specific embodiments.

Definitions are provided below to further illuminate specific embodiments. These definitions may pertain to specific exemplary embodiments and therefore should not be seen as limiting.

Cumulative sucking effort: the sum of intra-oral pressures achieved during either a long- or short-term effort (e.g., during a burst of sucks per unit of time or volume consumed).

Orogram[$_{SB1}$]™, a term at times used to describe tracings obtained by the Orometer.

Orometer™, a novel device to electrically record and measure feeding activity as described herein.

Orometry™: the measurement, quantitation and analysis of physical data obtained during nutritive feeding, including pressure, continuous flow, and physiologic measures of muscle activity, breathing, deglutition, etc.

Sucking efficiency is defined with regard to volume/time or volume/number of sucks.

Sucking effort describes negative intra-oral pressures achieved by an infant during feeding. This is recorded for each suck at high enough resolution that the measurements are effectively instantaneous in comparison to the physiological events under observation. In using this term, positive pressures are excluded and do not imply a maximal sucking force.

Overview

Feeding problems are a frequent harbinger of occult or nascent neurological damage and are a major obstacle in transitioning infants from hospital nursery to discharge. Severe problems often require repeated hospitalization and tube feeding. Refractory feeding problems contribute significantly to the high cost of health care. Dysfunctional sucking in the newborn, in the absence of any focal neurological symptoms, has been reported to correlate with developmental delay evident at 24 months of age. It is estimated that 57-92% of infants with brain damage have dysphagia and are at higher risk of long-term malnutrition, growth failure, and higher mortality rates. Early, accurate diagnosis of feeding problems would be of great help to these infants, as they could then receive the most appropriate treatment at an earlier age. Furthermore, because sucking behavior changes as infants mature, accurate measurements can detect changes over time in a way that can be used to develop a scale of oro-motor development.

As the population ages, feeding problems in adults are also becoming more prevalent. Many of the methods herein described, with specific embodiments, are relevant to the study and clinical characterization of feeding in adults, the elderly, and even to animal feeding, including (without limitation) new veterinary applications.

In human neonatology, one concern is determining when a pre-term infant is strong or healthy enough to feed on its own and to be discharged from a neonatal intensive care unit. The Orometer feeding observation device as described in the references assist clinicians in determining the feeding ability and health of an infant and may help diagnose feeding problems or other conditions. Common clinical practice uses qualitative measures of infant strength and feeding ability, such as the NOMAS rating scale, but, according to specific embodiments, systems and methods as described herein provide quantitative measures of feeding activity, strength and ability; they can determine baselines for feeding behavior in healthy, full-term infants and also pre-term infants who are healthy apart from prematurity.

Feeding monitor systems (one example of which is referred to as the Orometer™) effectively measure nutritive sucking behavior for healthy full-term infants, premature infants, infants with feeding problems, infants with serious illness, and any other human or animal subject where it is desired to study feeding or sucking behavior. In various configurations, feeding monitor systems can provide a quantitative and permanent record of sucking comparable to EEG, EKG, or EMG that is of value in supplementing the current scoring tools used to assess an infant's feeding competence prior to discharge and for predicting long-term outcomes.

In various configurations and according to specific embodiments, analysis methods and systems as described herein can be used with or incorporated into a device that is portable, noninvasive, and produces durable, reliable records of pressure changes and fluid flow that occur during infant feeding.

According to specific embodiments, methods and systems as described herein can provide real-time values or signals that accurately correspond to or characterize feeding or drinking activity. According to specific embodiments, collected monitoring data can be analyzed immediately at the time of collection. Previously recorded data can also be analyzed as described herein. The resulting records provide value to feeding researchers and all professionals who evaluate feeding, including without limitation pediatricians, nurses, speech-language pathologists, occupational therapists, caregivers and others. The methods described herein can provide various quantitative measurements of oral activity; permitting individual humans or animals to be studied and compared using precisely-described parameters as well as qualitative characterizations of oral activity.

In the examples displayed in the application, the Orometer is in essence an infant feeding bottle fitted with a chamber behind the nipple that contains a pressure sensor. As the infant feeds upon the bottle, pressures in the chamber are measured. These pressures are typically negative, in the range of zero to about 50 mm of Hg. In specific example systems, the signal is sampled at a rate of 1 KHz at the time of collection, but for convenience, the data can be subsequently down-sampled (e.g., "decimated") to a sample rate of 100 Hz (since infant sucking is typically focused at 1 Hz, or one suck per second, this provides ample resolution for data analysis). Typical data sets (which can be represented by an array of values, tracings, or signal graphs or curves) produced by this system provide a characteristic signal with downward pressure deflections representing individual nutritive sucks, further described herein. (While the data sets described herein are generally described as ranging from neutral to negative values, indicating sucking, it will be understood that other systems may be designed to display positive values, or an absolute value of the data may be used.) In particular example systems, data is commonly collected for 5 to 15 minutes.

Other example devices that may generate data that can be analyzed as described herein for measuring the pressure produced by infant sucking. These include the Kron nutritive sucking apparatus (a burette fitted with a pressure sensor) to study infant feeding behavior. A similar device, referred to as a Medoff-Cooper nutritive sucking apparatus has been described. Another approach involves a pacifier equipped with a pressure sensor known as an NTrainer™; this device is also equipped with a computer controlled air pump that provides gentle stimulation in the form of pulsations to the nipple, which prompt feeding behavior. Other work involves direct measurement of intraoral pressures, using a tube in the oral cavity. Other systems described in the literature including in the listed references may also generate initial data sets as described herein.

Analysis of the data produced by the Orometer or other devices for measuring feeding data presents a number of challenges, among those are event identification (in some earlier work referred to as feature identification), in particular the identification of individual nutritive sucks and the determination of suck bursts, and measurement of features to characterize the strength and consistency of infant feeding.

The problem of identification of individual nutritive sucks in the data is complicated by several factors. These include a substantial range in amplitude of deflections found in the data, both between subjects or test sessions. Another problem is ambiguity: some data files display complex waveforms where it isn't clear where one deflection (nutritive sucking event) begins, and the next one ends. Some data files exhibit large deflections that are bimodal—containing sub-deflections—and this leads to difficulty in setting an amplitude criterion for suck identification: a criterion high enough to exclude these sub-deflections may be too high to detect smaller deflections that stand alone, apart from larger deflections.

According to specific embodiments, methods and related systems as described herein address these challenge to provide improved diagnostic or analytic operation. One or more feature detection techniques, some similar to those commonly used in signal analysis but unique in the analysis of feeding, are applied to the data. These techniques include one or more of (1) smoothing the signal and then (2) scanning for zero-crossings of the derivative of the signal (where the slope changes from negative to positive). According to specific embodiments, a two-pass strategy is used, (3) first identifying the larger deflections, and (4) then identifying smaller deflections that are not superimposed upon the larger deflections. According to specific embodiments, the diagnostic technique can be referred to as suck recognition.

Further, one or more burst-identification methods are applied. One criterion is to look for gaps between sucks (suck intervals), that in specific applications are typically four seconds or greater, measured peak-to-peak for consecutive sucks. Other intervals can be used according to specific embodiments and have been proposed in other work. The distribution of suck intervals has shown that within a limited range the exact criterion is arbitrary. In fact, there can generally be more gaps between sucks slightly smaller than any chosen burst criterion than slightly larger than that burst criterion. So in examining tracings with bursts indicated, it will generally seem that there are gaps that are a bit too short to be counted as a burst pause.

According to specific embodiments, sucks are measured in one or more novel ways to provide further data regarding feeding. Measures of sucks according to specific embodiments can include suck amplitude and the area enclosed inside the suck. These are generally measured from neutral, zero pressure (occurring between individual suck events). However, there is often wander in the baseline, or offset, and the amplitude of these deviations from wandering is typically similar to the amplitude of the sucking itself. To address this, according to specific embodiments a proxy baseline is generated for neutral pressure that will follow the bases of sucks if baseline wander or offset is present.

In further embodiments, the difficulties in suck identification and burst identification prompted the development of an alternative approach to characterizing or measuring infant feeding, an approach not dependent on identification of sucks or bursts. This approach includes proxy measures of feeding persistence or number and duration of bursts, such as fraction of time showing feeding behavior. One proxy measure for amplitude or area of sucks is integrated area of sucking; this can also be expected to correlate with the volume consumed by the infant. According to specific embodiments, novel aspects of these alternative approaches can be used apart from previously-described methods (stand-alone), or in combination with them.

Clinical studies suggest that it would be desirable to characterize infant feeding behavior that is regular and consistent by using quantitative methods that distinguish it from irregular, or inconsistent feeding behavior. According to specific embodiments, methods as described herein provide this. These include variability of suck amplitudes during a suck burst, or variability of suck intervals in a suck burst. The number of bursts and their durations are measured as an indication of halting, which may be caused by neurodevelopmental problems, other medical conditions, or fatigue in feeding. Non-suck-based measures of feeding consistency were also developed. These were based on a measure of the concentration of the Fourier Transform about the primary frequency of feeding; a high concentration of the Fourier Transform is indicative of a strongly rhythmic feeding pattern.

Detailed DESCRIPTION OF METHODS

Feature (Suck) Identification

As discussed herein, the Orometer and other such measurement devices produce pressure data as a function of time. If these are plotted, tracings are seen showing pressure changes due to the infant's sucking; individual sucks appear as downward deflections in the tracing. FIG. 1A is a data plot of a 10-second extract of one test session illustrating one type of example data as discussed herein.

Figure 1B:
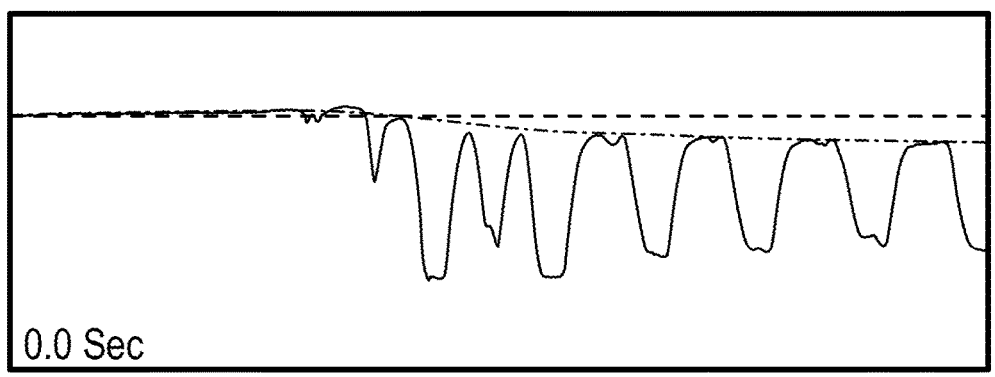

Using data roughly of this type, one method according to specific embodiments is to identify each suck in the data file and measure it. According to specific embodiments a baseline is determined as a proxy for the neutral pressure e.g., 0 mm of Hg. This can be performed using a straightforward process of computing a "running maximum" curve and then smoothing it. The result is a baseline curve that runs along the shoulders of each deflection as shown in FIG. 1B. This is done to offset or correct baseline drift or wander that can be present in Orometer and similar tracings. The baseline curve may be termed a "suck-pressure baseline".

Figure 1C:
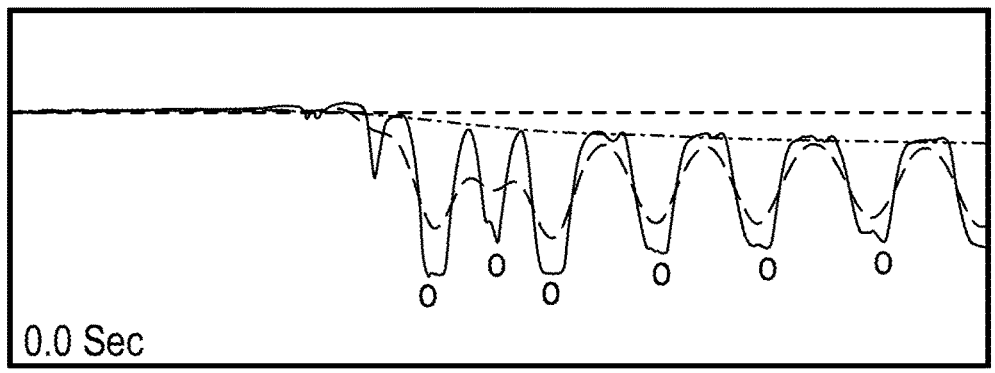

With the baseline established, event identification (or feature identification) is performed. According to specific embodiments, this uses a signal analysis technique of performing a running average of the data. An example running average is shown in FIG. 1C. The sucks are identified as local minima of the smoothed curve of sufficient amplitude (measured against the baseline curve). Identified sucks in this analysis are marked with small circles in FIG. 1C.

Figure 1D:
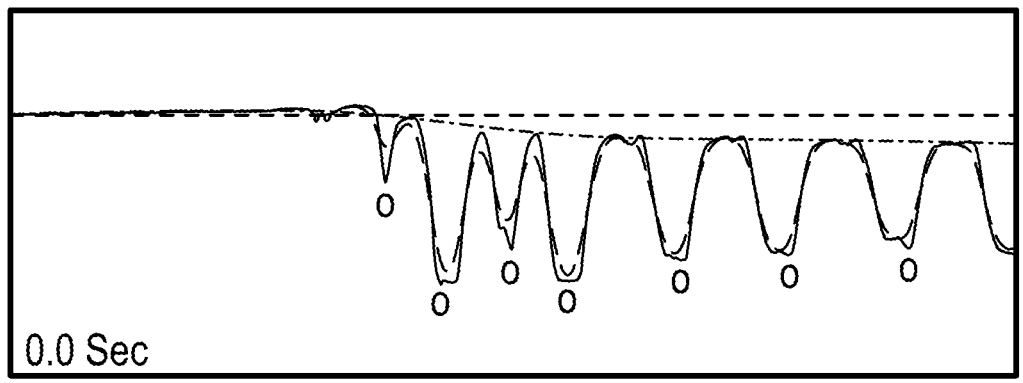

According to specific embodiments, the smoothing process is tuned to avoid identifying bimodal shapes sometimes found in larger deflections as separate sucks; it ignores smaller deflections. But this will sometimes result in missed small deflections, as illustrated in the figure with the initial deflection. According to specific embodiments, a second pass [$s_{SB5}$] is employed with the smoothing process tuned to produce a smoothed curve that follows the tracing closer, to find smaller deflections; if these are within the bounds of already-found larger deflections, they are ignored. FIG. 1D illustrates the second smoothed curve and illustrates that the initial deflection is now marked as a suck.

Figure 2:
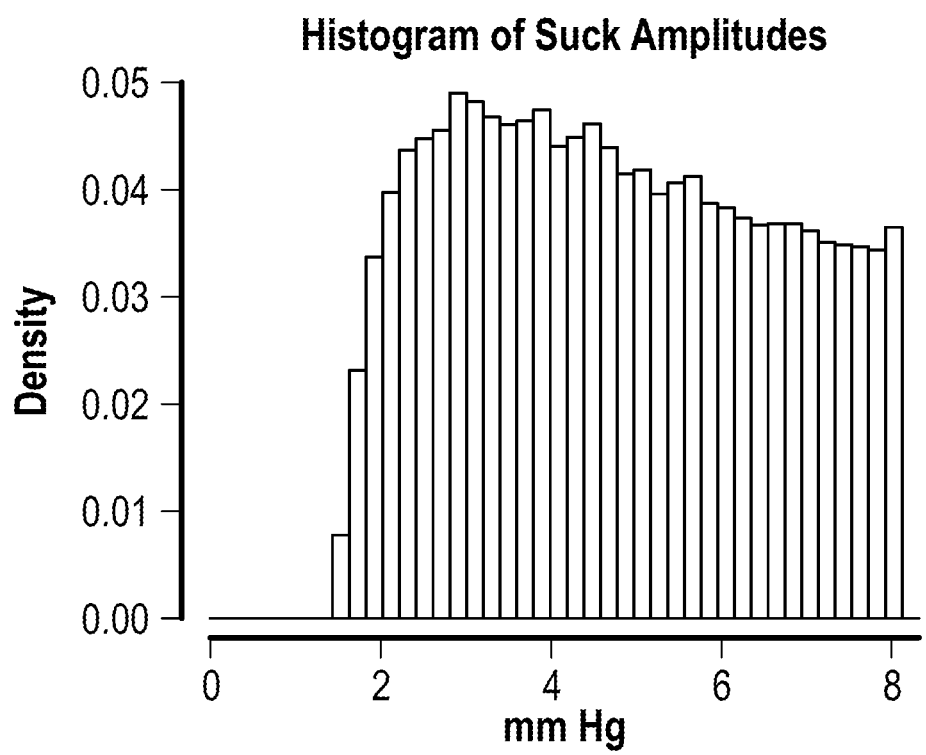
FIG. 2 is a density histogram which shows that almost all infant sucks are greater than or equal to 2 Torr.

According to specific embodiments, methods and systems are developed to determine when a deflection in pressure in feeding data constitutes a suck. As an initial criteria, according to specific embodiments, a suck was defined as a deflection of at least 2 Torr (mm Hg) negative pressure (measured from a baseline as discussed herein, rather than from 0 Torr pressure). This decision was based upon observation of infant behavior, as seen in video records of Orometer test sessions: deflections that appeared to be the result of infant sucking were of amplitude 2 Torr or greater. It turns out that in some investigations so far this is a natural cut-off in amplitude for sucks; there are few deflections smaller than 2 Torr but many deflections from that level on up. This is seen in the density histogram of FIG. 2.

Observations have indicated that only 1.3% of all deflections are below 2 Torr in amplitude. This initial result is based on 328,386 deflections found in a total of 1,011 data files. According to specific embodiments, the actual criteria for when a deflection is identified as a suck is part of the algorithm used to find the sucks, as described herein. Thus, not every deflection of 2 Torr will be identified as a suck. According to specific embodiments, a minimum area criterion can be used to avoid deflections resulting from instrument artifacts (such as very thin spikes due to electronic noise). Instrument artifacts of this kind are very rare, but more common are large deflections (clearly resulting from infant feeding) that have "sub-deflections" (bimodal peaks or small bumps often seen at the beginnings of deflections). A simple amplitude criterion high enough to not count these sub-deflections will miss many small deflections that are clearly individual infant sucking events.

In earlier work, software with a graphical user interface that allowed human correction of software-based automated suck identification was used (this program at times was referred to as "Suck Editor"). Manual suck identification was determined to be less desirable because objectivity and consistency of suck identification could not be guaranteed. Thus specific embodiments provide methods for automated suck detection.

In particular embodiments, larger deflections are found first, and then smaller deflections are located that are not within the bounds of larger deflections. Human inspection of the results indicates occasional deflections that are questionable (false positives or false negatives as sucks), but some data files show confusing 'chaotic' tracings. In such cases it is not always clear (even to a human expert) how to cut the tracing into individual deflections. Fortunately, such ambiguities affect a fairly small fraction of deflections (5% perhaps), and the gain in consistency outweighs the disadvantages. A purely human suck-identification system would probably have as high an error rates due to the ambiguity of some tracings and it would be intensely labor dependent.

Thus, according to specific embodiments, an improved automated suck identification method is provided. This provides substantial benefits in feeding analysis.

Suck Measurement

Figure 3A:
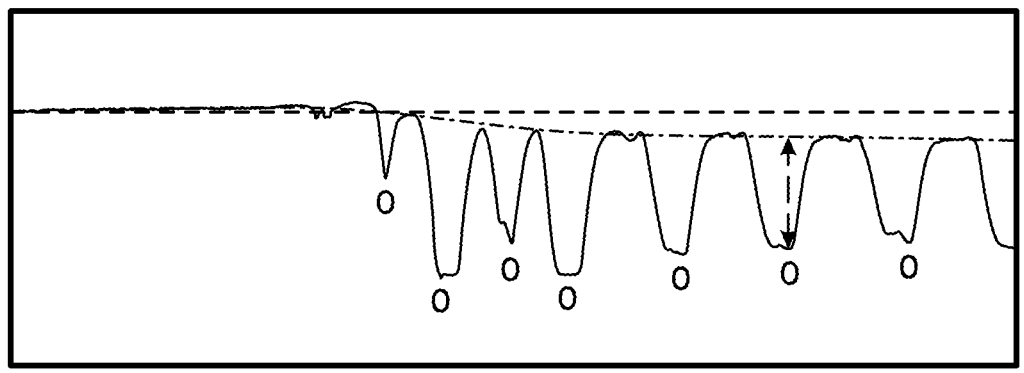
FIG. 3A-E are graphs illustrating captured data and data analysis for automatic suck measurements according to specific embodiments.
Figure 3B:
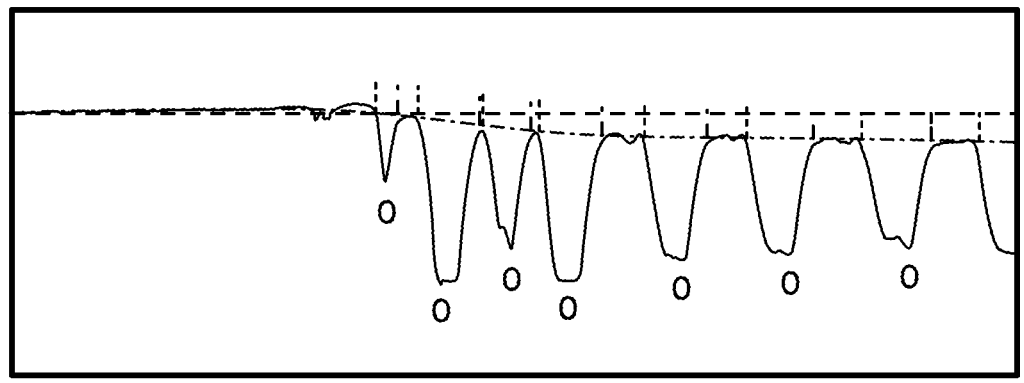
Figure 3C:
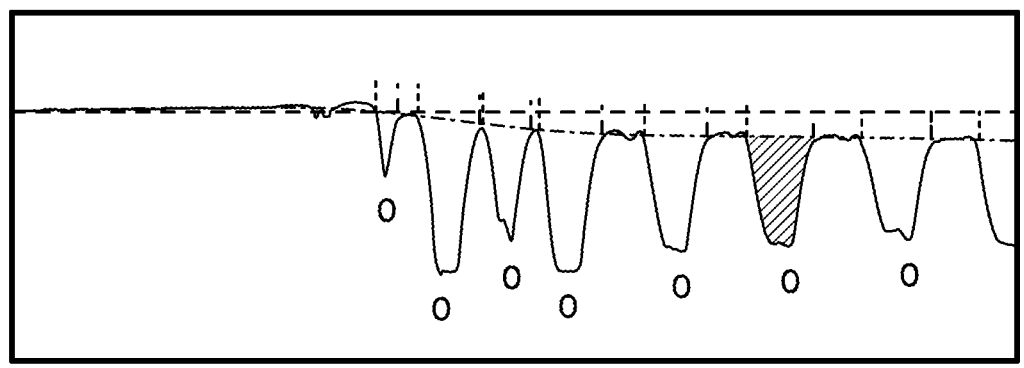

According to specific embodiments, a number of suck characteristics can be automatically measured and output with suck identification. The amplitude of the suck is measured from the maximum negative pressure of the suck (e.g., its downward-pointing peak) to the baseline curve, for example in units of Torr (mm of Hg). FIG. 3A shows an example measurement indicated by the double arrow. To find the area of each suck, the method first marks the beginning and end of each suck (using a simple proximity criterion of the tracing to the baseline curve). Here, these are marked with tick marks as shown in FIG. 3B. The area of the suck is determined according to specific embodiments by integrating between the baseline curve and the tracing. In this example, the units are in Torr-sec. (For example, a suck that has an average pressure of 24 Torr of pressure for 0.75 sec would have an area of 24×0.75 Torr-sec.) FIG. 3C illustrates one measurement of the suck area.

Figure 3D:
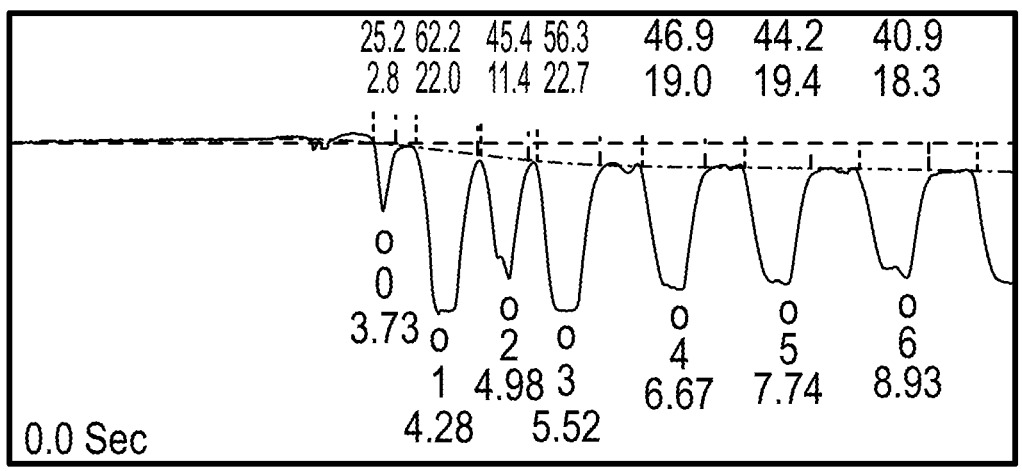

FIG. 3D displays measurements for each suck in a specific example. In the figure, each suck is labeled below its tip by the suck number (beginning with 0), and with the time in seconds when the peak negative pressure occurred. The two numbers above each suck on the top of the frame give respectively the amplitude in Torr and the area of the suck in Torr-seconds.

Figure 3E:
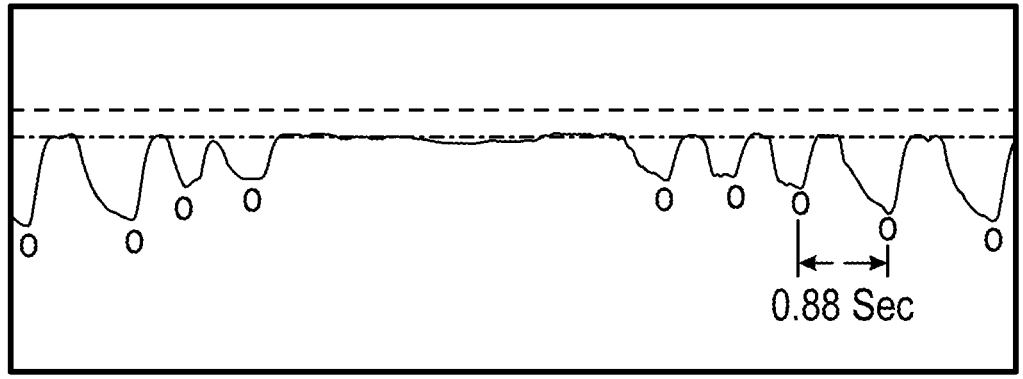

According to specific embodiments, the annotated tracing in FIG. 3E was produced automatically by the suck-identifying software. Similar annotated tracings can be produced for every data file, displaying for the entire data file the information shown in the figure. (Such annotations are useful for clinicians in some circumstances, and they also enable verification of the algorithms used by the software, expediting debugging.)

Burst Identification

Figure 4:
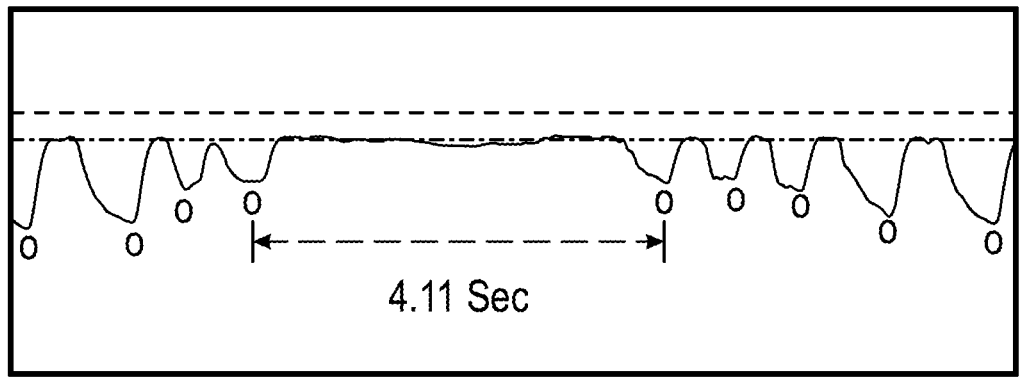
FIG. 4 is a graph illustrating captured data and data analysis for automatic burst identification according to specific embodiments.

Infant feeding is typically interrupted by pauses that separate groups of sucks into suck bursts. Burst identification is based on suck intervals. A suck interval is the duration (in sec) from one suck peak to the next suck peak. An example is shown in FIG. 4. According to specific embodiments, a group of sucks is divided into two bursts if the suck interval is greater than a specified threshold, such as 4 sec. In specific embodiments, the criterion of about 4 seconds peak-to-peak is chosen to match a commonly used criterion of 3 seconds between sucks. (Because sucks are typically about 1 sec in duration, 4 seconds peak-to-peak will result in at least 3 seconds between the end of one suck and the beginning of the next suck.) According to specific embodiments, this threshold value can be adjusted in various situations.

Thus, as discussed above, one of the criteria used for separation of suck bursts (separate groups of sucks) can be a suck interval of 4.0 seconds or greater. In a specific example, this is measured from peak negative pressure of one suck to the peak negative pressure of the following suck. This criterion for separation of suck bursts generally follows portions of the reviewed literature, where generally no activity of 3 seconds or more is used. Generally, a 4 sec criterion allows for average suck width of about 1 sec. But this criterion is somewhat arbitrary, and due to the statistical distribution of suck intervals, there will always be more suck intervals that fail to meet the criterion for a suck burst than do meet the criterion, no matter which criterion is chosen.

An alternative variable can be used as a proxy for number of bursts, mean length of bursts, or mean number of sucks per burst: the fraction of time showing activity. This was computed by cutting the time interval under analysis into 1-sec subintervals, and seeing which fraction of these show integrated areas of at least 1 Torr-sec. This statistic does not depend on an arbitrary choice of the suck burst separation criterion, but it is closely tied to statistics based on burst number or length.

Measures of Disordered Feeding

According to further specific embodiments, methods and systems as described herein can produce measures of disordered feeding or feeding that is irregular; including (but not limited to) instances when an infant or other subject feeds in a faltering or non-rhythmic manner. This can be reflected in variability in suck amplitudes or spacing between sucks (suck intervals).

One measure is the coefficient of variation of suck amplitudes or of suck intervals. This is the standard deviation of these values divided by their mean. However, a sequence of sucks with gradually increasing amplitude might produce a relatively high coefficient of variation of amplitude without showing the kind of variability that would characterize disordered feeding. To address this, according to specific embodiments, another measurement is introduced: 'suck amplitude variability,' which is generally the standard deviation of ratios of amplitudes of consecutive sucks.

A pattern of feeding that might indicate fatigue or weakness is a suck-pause pattern, where an infant or other subject produces short suck bursts separated by numerous burst pauses. This can be assessed by counting the number of bursts, their duration in seconds, or their length (number of sucks per burst). Other measures of sucking consistency include the coefficient of variation of burst pause duration, or the coefficient of variation of burst durations or lengths.

Fourier Transforms

A more sophisticated measure of irregular sucking patterns makes use of the Fourier transform, a mathematical tool for identifying the frequency of a periodic phenomenon. As is understood in the art, a strongly rhythmic phenomenon will have most of its energy concentrated near one particular frequency; the Fourier transform can be used to produce an 'energy spectrum' that shows this. But a phenomenon that lacks a clear rhythmicity will not have its energy concentrated near one particular frequency. The Fourier transform can show this, and this can serve as a measure of how regular or consistent an infant's sucking is. The following examples illustrate what the Fourier transform can indicate.

Figure 5A:
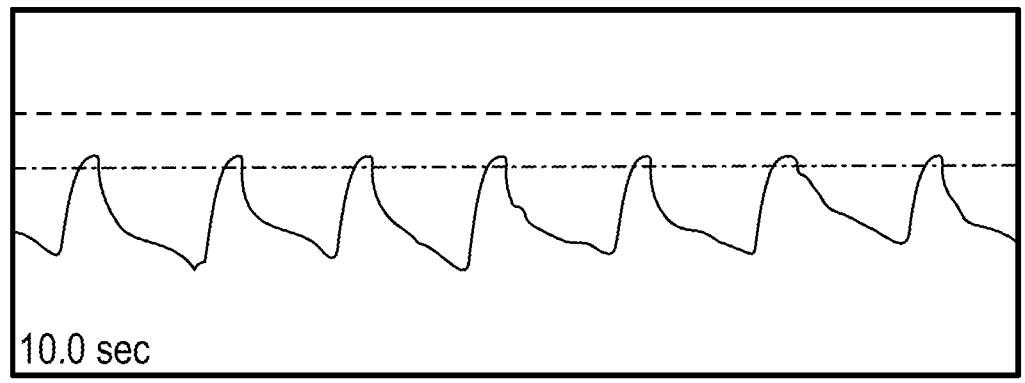
FIG. 5A-F are graphs of feeding activity with matched Fourier transforms, illustrating captured data and data analysis to determine feeding patterns according to specific embodiments.
Figure 5B:
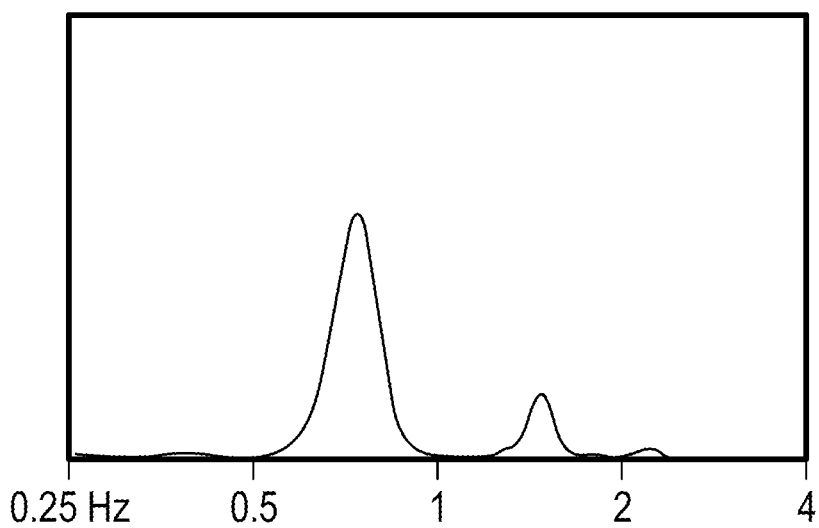

FIG. 5A-F are graphs illustrating captured data and data analysis to determine feeding patterns according to specific embodiments. The Fourier transform finds the frequency content in a signal. For example, consider the 10-second extract from an Orometer tracing in FIG. 5A. This extract shows about 7 sucks in 10 seconds, which is a frequency of sucking of about 0.7 sucks per second. The Fourier transform is shown in FIG. 5B.

Figure 5C:
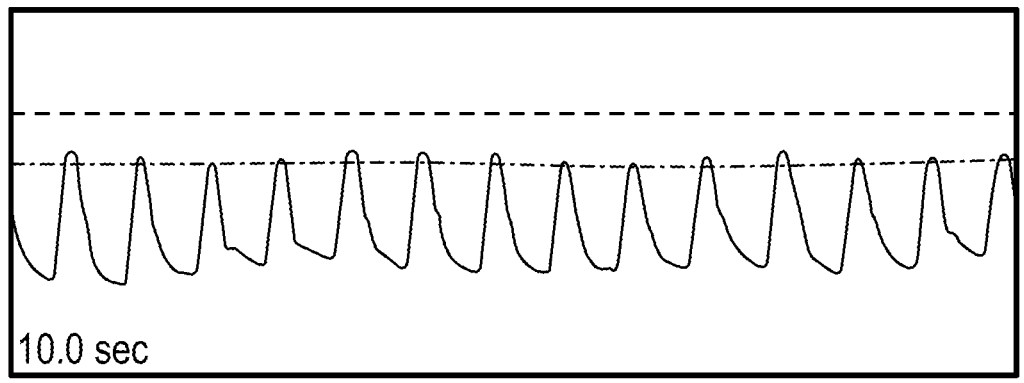
Figure 5D:
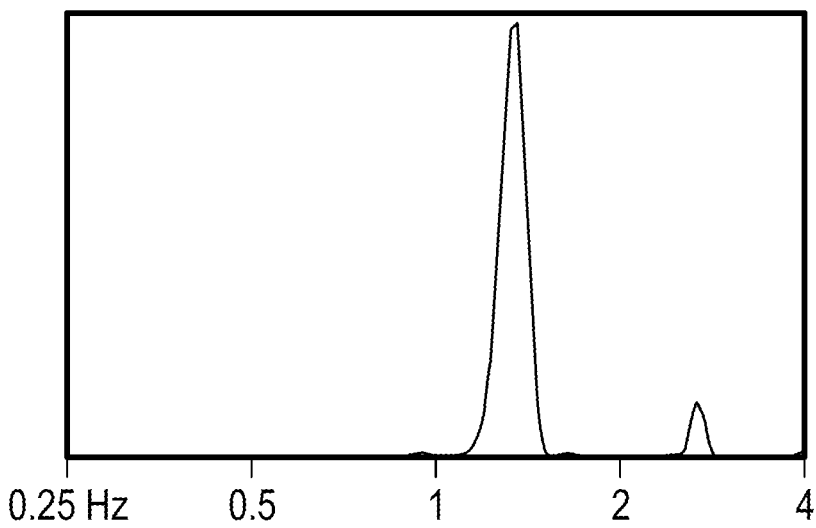

This shows the peak at 0.74 Hz, which indicates that the sucking is at a rate of 0.74 sucks per second (7.4 sucks in 10 seconds). Here, there is a second peak at twice the frequency, or 1.5 Hz; this is typical (it reflects the irregular shape of the waveforms in the example Orometer tracing). A further example is shown in FIG. 5C, which shows a much faster rate of sucking, about 14 sucks in 10 seconds, or 1.4 sucks per second as indicated in the Fourier transform illustrated in FIG. 5D, showing the peak frequency is 1.35 Hz.

Figure 5E:
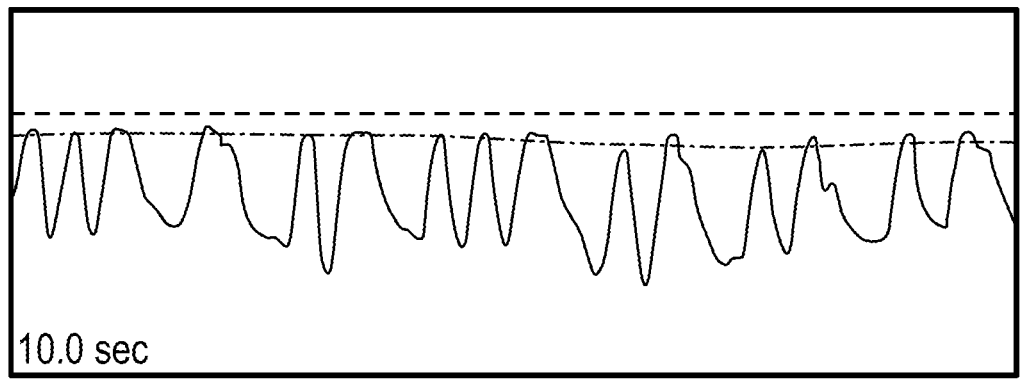
Figure 5F:
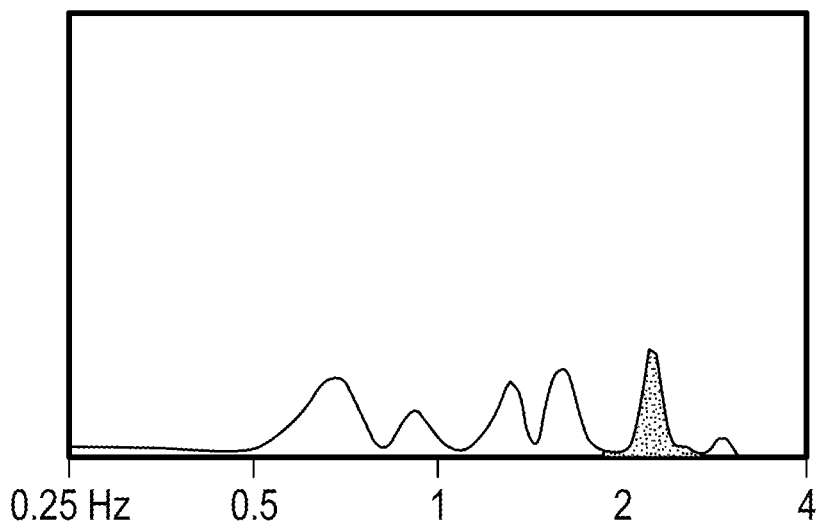

If feeding is disordered, there generally may not be a clear-cut frequency of sucking established. The Fourier transform can detect this. FIG. 5E shows a tracing showing sucks of uneven durations or spacing. The Fourier transform illustrated in FIG. 5F shows several different peak frequencies, none of which dominate.

According to specific embodiments, a Fourier Transform frequency analysis as illustrated in the examples is used as a measure of disordered sucking: Consider the proportion of the area under the Fourier transform curve that is near the peak frequency (here, shaded). If most of the area is under the peak frequency, this signifies strongly rhythmic feeding, but if the frequencies are spread out as shown in FIG. 5F, this indicates feeding that is less rhythmic or ordered. This can occur (as in this example) because the spacing or durations of sucks change, or because suck amplitude changes substantially.

In further embodiments, a Fourier transform can be used to count sucks. For example, if the Fourier transform indicates a rate of 1.4 sucks per second for 10 seconds, this would imply 14 sucks in that 10-second interval. The correlation of these Fourier-inferred suck counts with direct suck counts is often very high (over 90%); if sucking is intermittent or suck bursts are very short, the correlation is less strong.

According to further specific embodiments, the Fourier analysis as described herein is performed by software or other logic analysis in conjunction with an Orometer in real time, allowing rapid display of diagnostic or other data. Example embodiments can analyze a data file in real time, or nearly in real time, with, in some embodiments, the baseline-finding process using a few seconds (e.g., less than about 5-10 seconds) of data to find the baseline and then identify and measure sucks.

Variables That Do Not Require Identification Of Sucks

Further work was directed to develop variables that do not require identification of sucks. One variable developed is to compute the area between the tracing and the baseline curve, for the entire time interval under analysis (e.g., the first 5 minutes of organized feeding activity). In general, the amount of fluid consumed is roughly proportional to the area.

In further embodiments, the difficulties in suck identification and burst identification prompted the development of a different approach to characterizing or measuring infant feeding, an approach not dependent on identification of sucks or bursts. This approach includes proxy measures of feeding persistence or number and duration of bursts, such as the fraction of time showing feeding behavior. A proxy measure for amplitude or area of sucks is integrated area of sucking; this can also be expected to correlate with the volume of fluid consumed by an infant or other subject.

[SB10]

Display Suck Inconsistency/Irregularity/Disorder

Figure 6A:
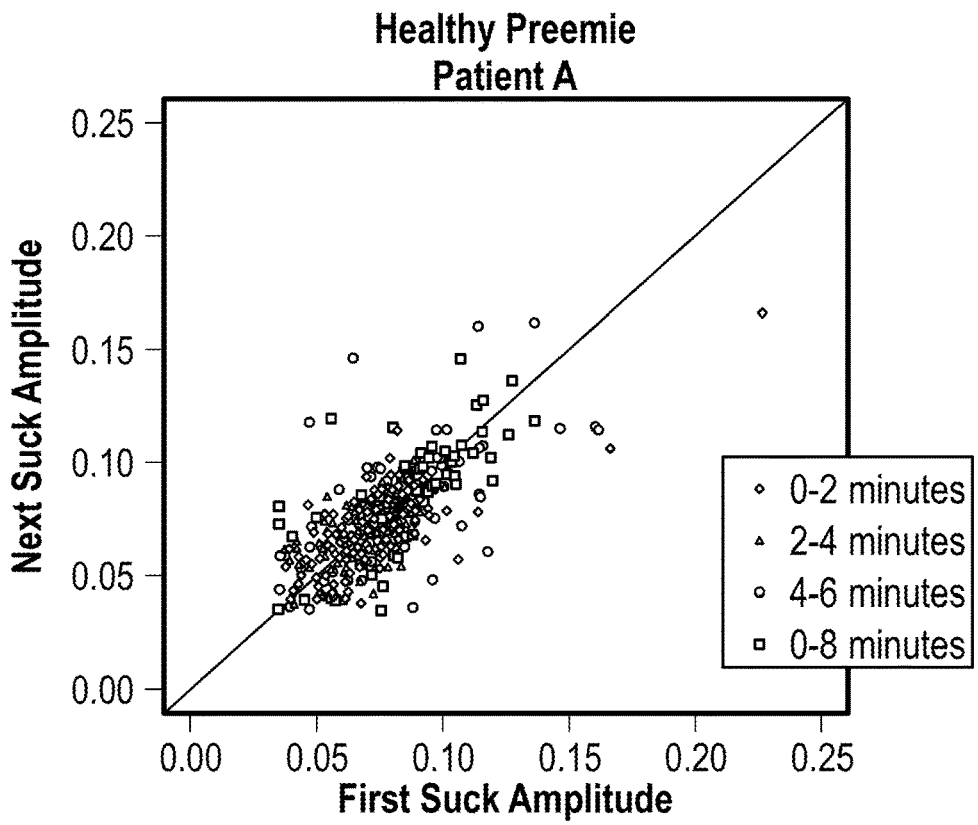
FIG. 6A-B are specialized scatterplots illustrating analysis to determine feeding patterns and quantify the consistency of sucking according to specific embodiments.
Figure 6B:
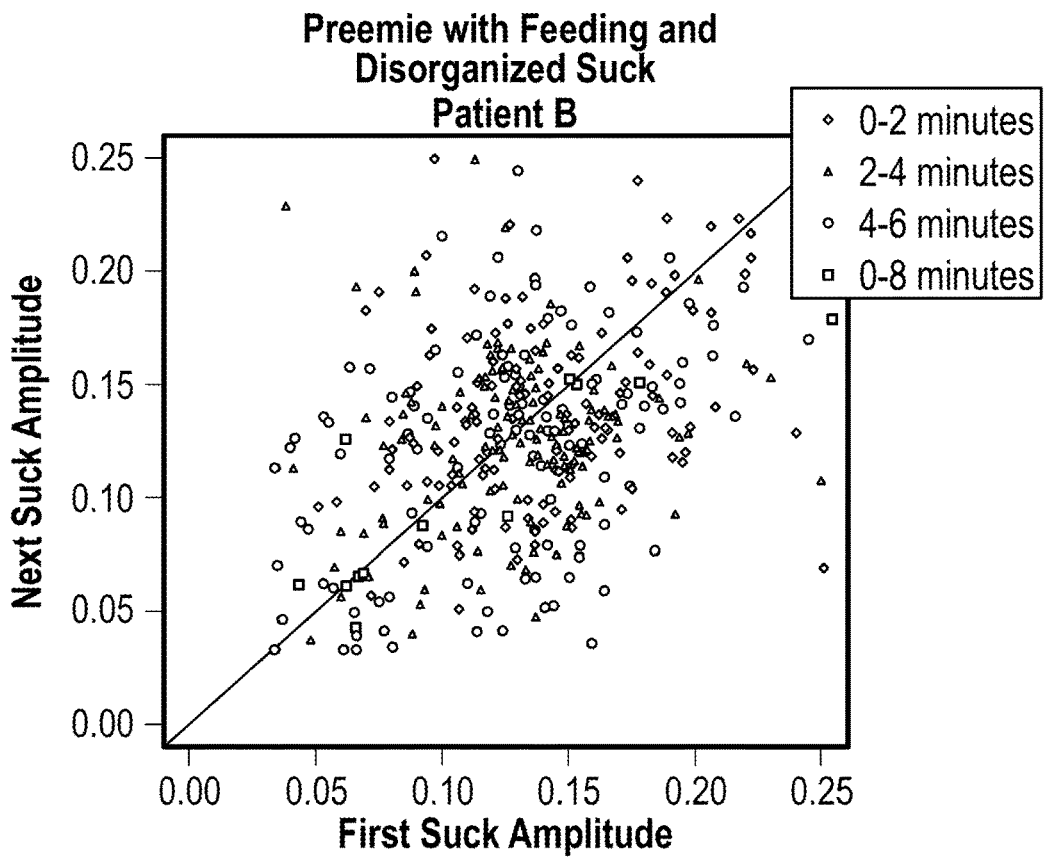

Scatterplot Chaotigrams: According to specific embodiments, a scatterplot chaotigrams method can be used to display suck inconsistency along with measures of chaos. In FIG. 6A, a healthy preterm infant (Patient A4 is compared with Patient B a comparable preterm infant who has feeding problems and disorganized suck, shown in FIG. 6B. In this example illustration, suck amplitudes are displayed as voltage, which is converted to pressure (typically displayed in Torr).

In a scatterplot chaotigram, suck-to-suck changes in amplitude are examined by plotting each suck with the amplitude of the following suck. Each set of consecutive sucks is plotted as a single point (x, y). For example, if the first suck in the session is −25 torr (vacuum) and the next suck is −30 torr, the first point on the graph will be (−25, −30). If the following suck is −15 torr, then the next point on the graph will be (−30, −15). Each suck in the session is consecutively plotted in this way until all consecutive suck-pairs have been graphed.

If all sucks in the file are roughly the same amplitude, then they will all cluster along the line y=x. If the cloud of points spreads widely above and below the line, this indicates suck amplitudes that vary greatly from suck to suck. This appears to be one robust indicator of inconsistent or disorganized suck.

Suck Variability Histograms (Chaotihists)

FIG. 7A-D shows another approach for quantifying the consistency of sucking: histograms that show what percentage of the sucks differ by various given amounts from the following suck.

Figure 7A:
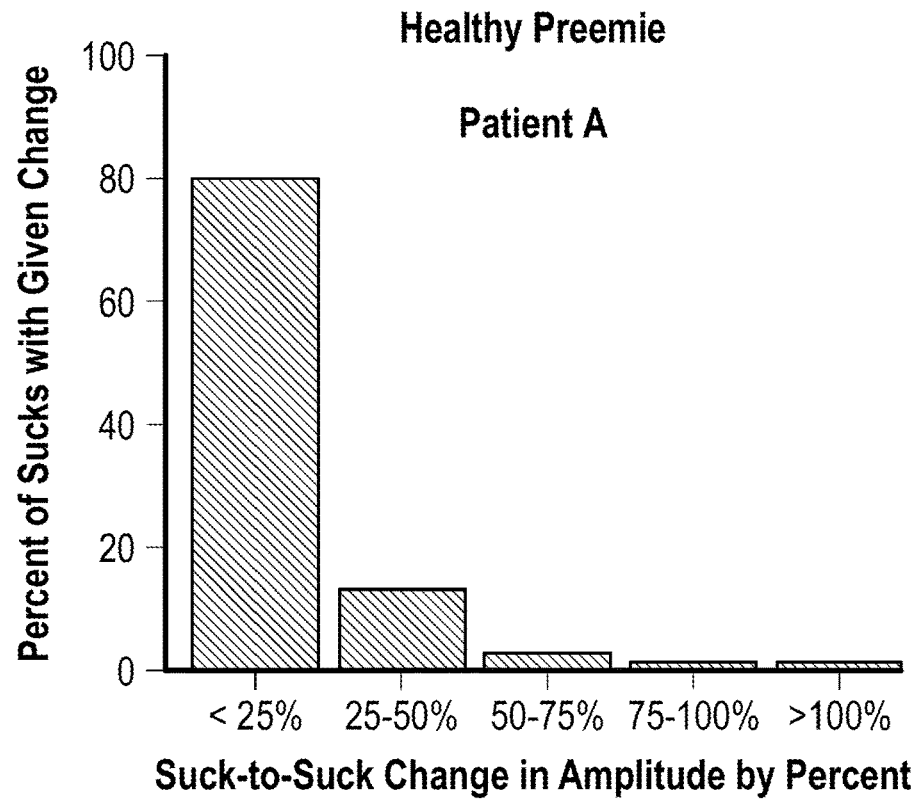
FIG. 7A-D are graphs illustrating analysis to determine feeding patterns according to specific embodiments. This illustrates another approach for quantifying the consistency of sucking: histograms that show what percentage of the sucks differ by various given amounts from the following suck.
Figure 7B:
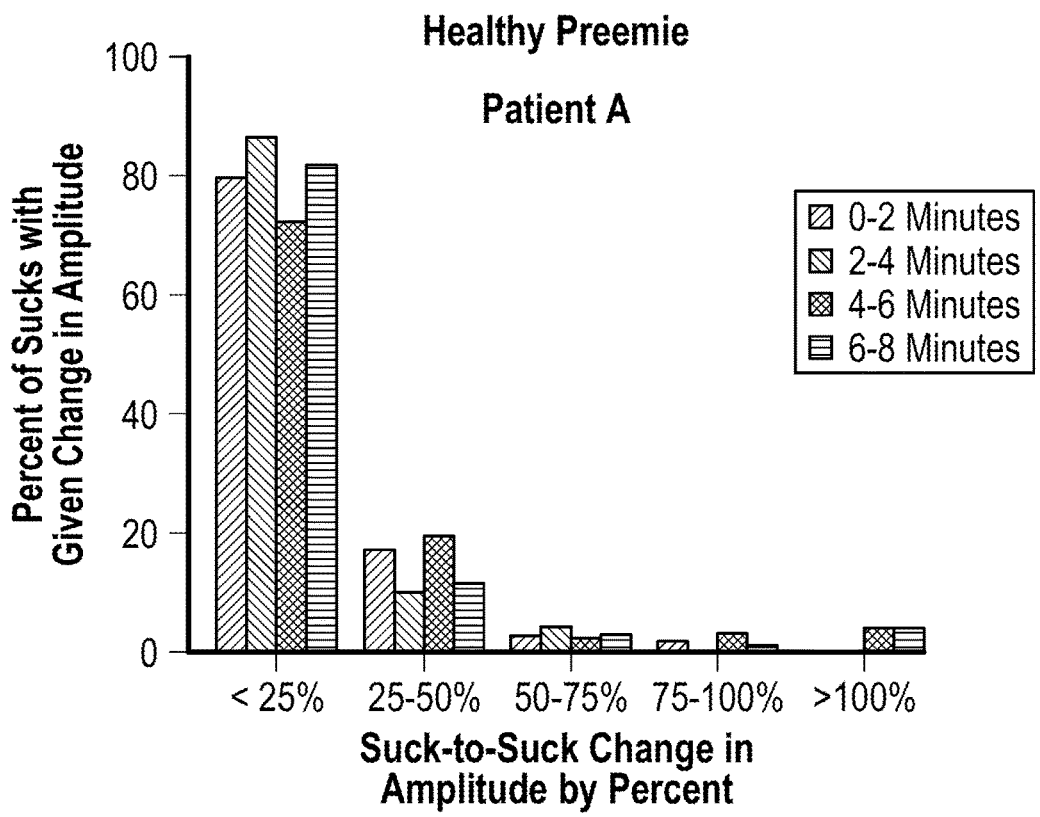
Figure 7C:
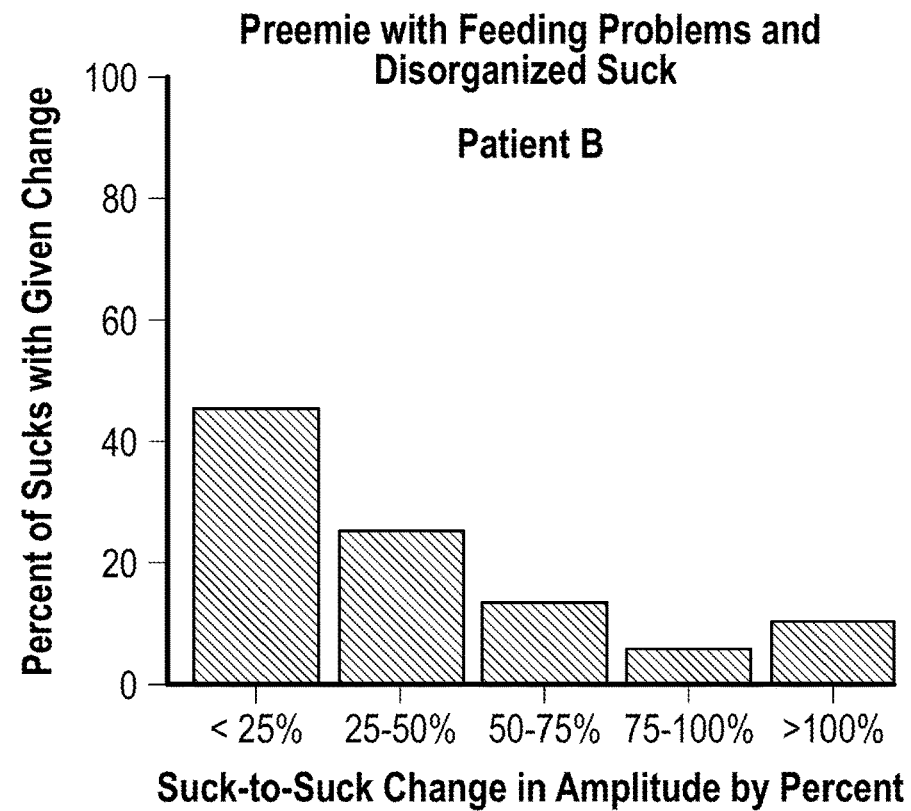
Figure 7D:
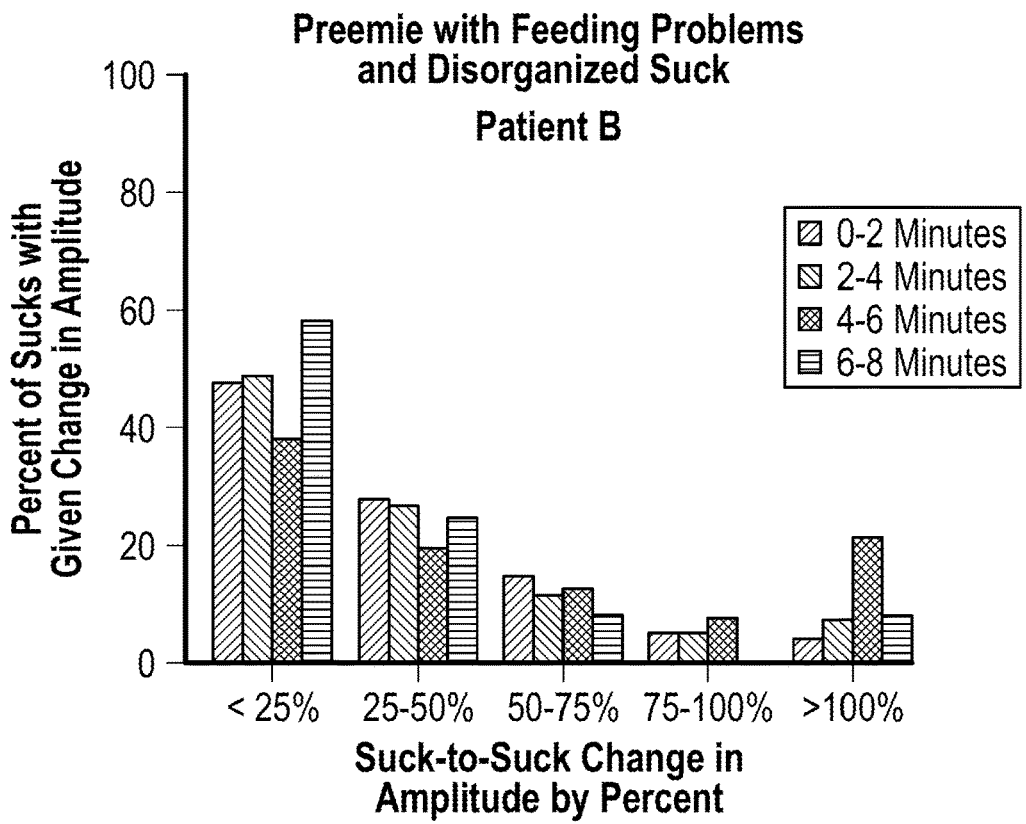

FIG. 7A shows the same patient and session shown in FIG. 7B (Patient A), a healthy preemie with consistent sucking. 70 to 80% of this infant's sucks differ by less than 25% from the following suck. FIG. 7B shows the same test broken into four 2-minute segments. FIG. 7C and FIG. 7D are comparable, but they were taken from Patient B, a preemie with feeding problems and disorganized suck. The chaotihist demonstrates that only 40% of this infant's sucks differed by less than 25% from the following suck, while 21% were more than 100% different. (This means that more than 21% of the sucks were at least twice as large in amplitude as the following suck or vice-versa.)

Stated differently, Patient A shows a very consistent pattern with ~80% of all sucks being less than 25% different and only a few sucks being more than 100% different. Patient B, in contrast, shows a very inconsistent sucking pattern in which ~45% of all sucks are less than 25% different while more than 50% vary by more than 50%; 21% of all sucks were more than 100% different. Patient A remained consistent throughout the whole session, whereas Patient B never developed a consistent pattern.

Example Systems

Figure 8A:
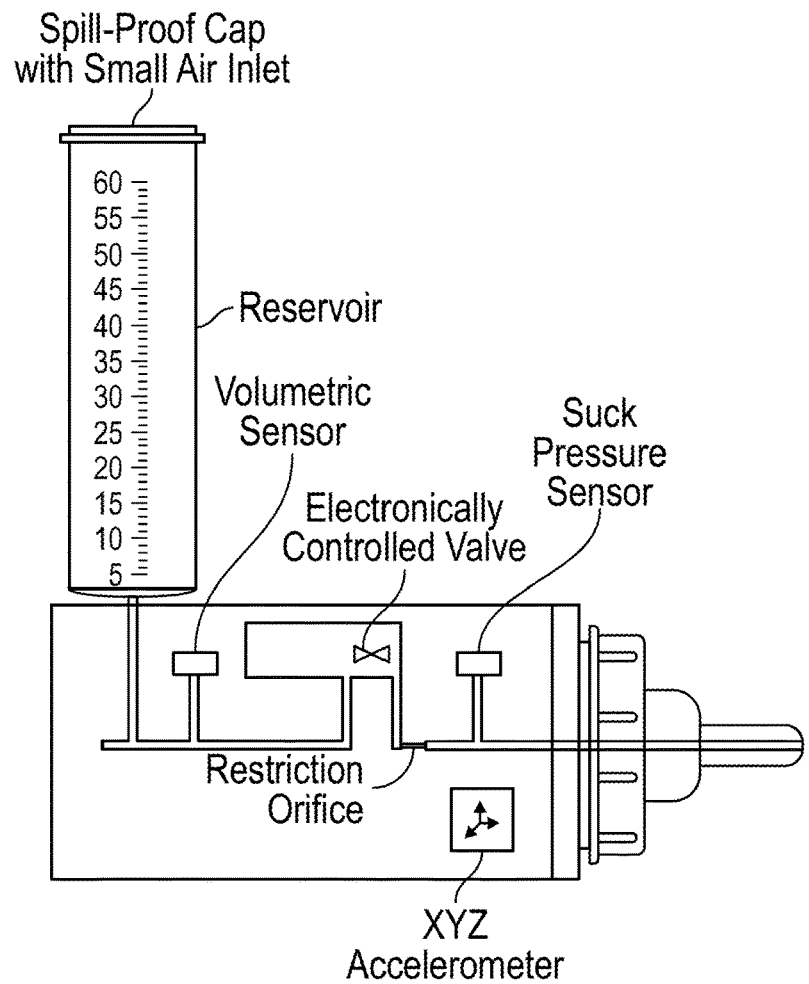
FIG. 8A-B are physical component block diagrams illustrating operational components of example systems as discussed herein. They illustrate various electronic and control aspects of two example apparatuses shown according to specific embodiments. (Note.
Figure 8B:
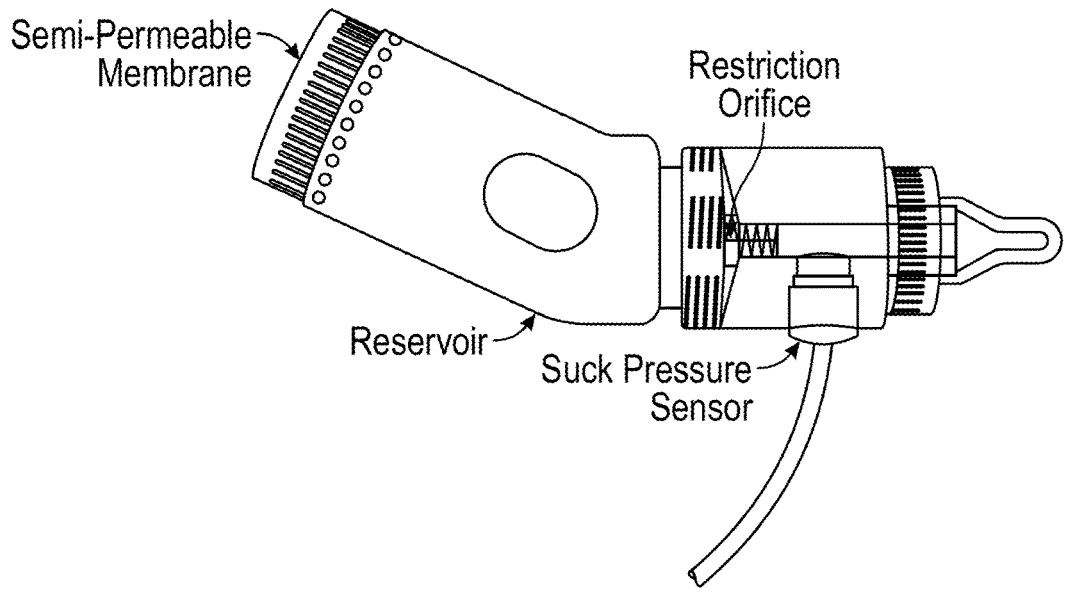
Figure 10:
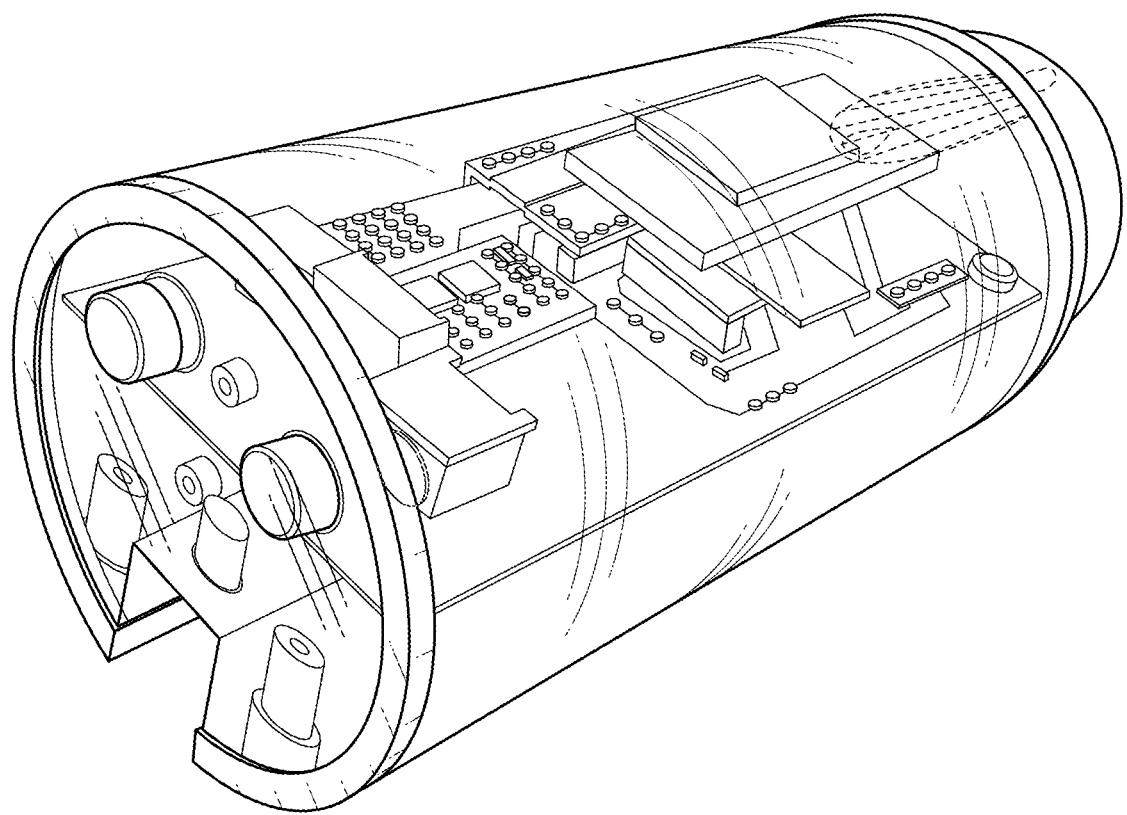
FIG. 10 is a photograph of an example working prototype. A Bluetooth™ module and processor board of a feeding monitoring apparatus is visible in outline through the transparent cover.

FIG. 8A-B are physical component block diagrams illustrating operational components of example systems. FIG. 8A is intended as an operational diagram and does not show relative dimensions of parts. FIG. 10 is a photograph of an example working prototype built with features shown in FIG. 8A. A Bluetooth™ or other wireless communication module and processor board of a feeding monitoring apparatus is visible in outline through the transparent cover. FIGS. 8A and 8B contain the following common features: the example apparatus includes a reservoir for storing a supply of a fluid, for example a liquid or semi-liquid drink or formula, and a flow chamber or flow path or flow channel. The flow chamber is operationally divided into two portions: the inlet portion receives fluid from the reservoir; the outlet portion is connected to an outlet, such as a nipple. A restriction orifice lies between the two portions and restricts fluid flow. An outlet is connected to the second end of the chamber to allow fluid to flow through the outlet portion responsive to vacuum or sucking force applied to the outlet. Since the outlet portion diameter is large in comparison to the restriction orifice diameter, sucking at the outlet can easily be measured by the suck pressure sensor connected to the second portion.

Figure 9:
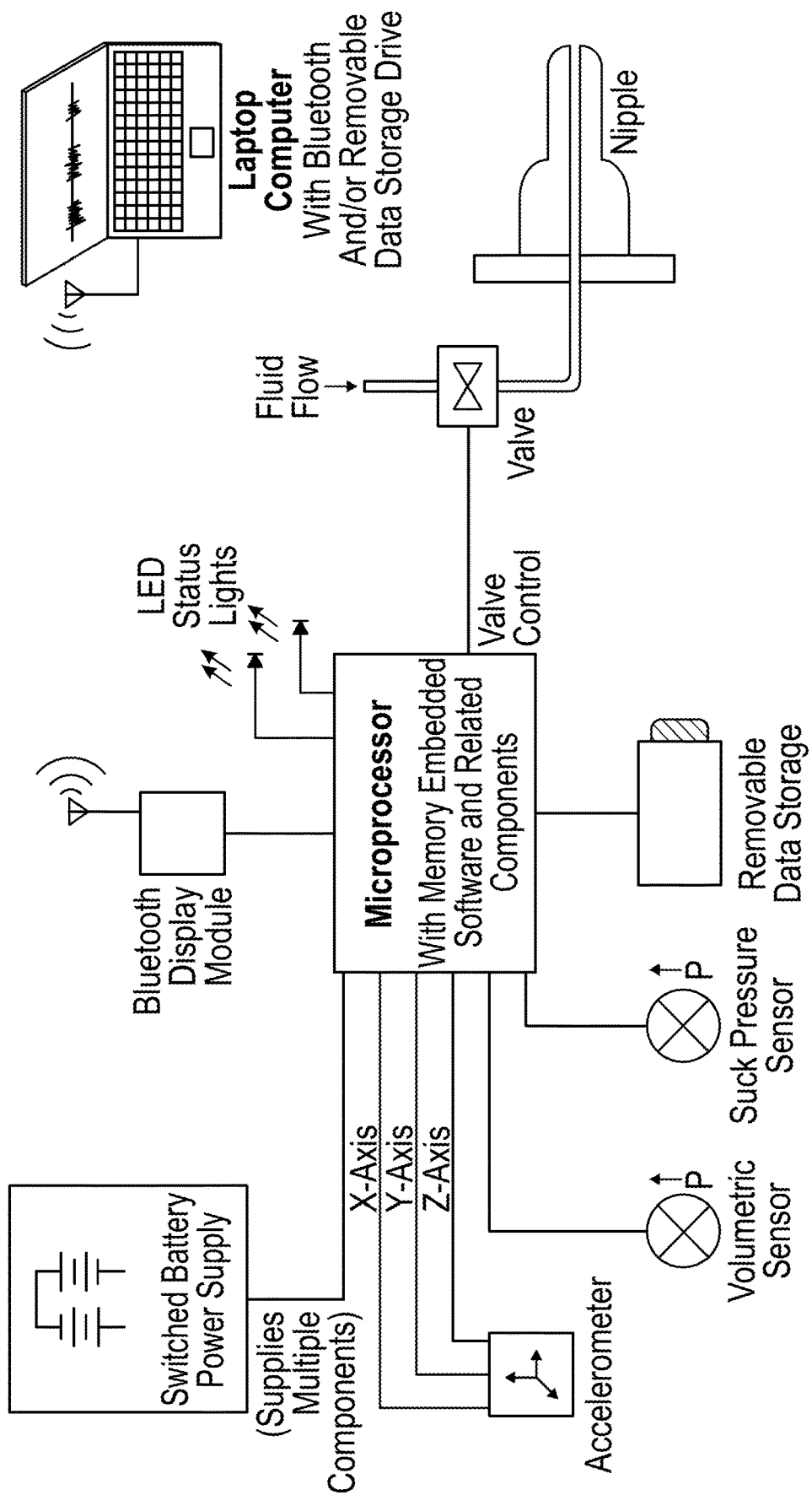
FIG. 9 is a block diagram illustrating various electronic and control aspects of an example apparatus.

FIG. 9 illustrates various electronic and control aspects of example systems. An apparatus as illustrated comprises three sensors: a suck force sensor, a volumetric sensor, and an optional accelerometer or position sensor generally providing data regarding X, Y, and Z orientation of the apparatus. As described below, the volumetric sensor measures the weight of remaining fluid in the reservoir. The accuracy of the volumetric sensor is enhanced when a pressure sensor is used in conjunction with an accelerometer or other position sensor that can be used to correct for individual vector components of fluid mass contained in the reservoir. A processor or controller reads data from the sensors and uses that data, and optionally also programmed data, to control a valve for regulated feeding. Optional elements comprise one or more displays or indicators on the apparatus and one or more interfaces for connecting to an external computing device. These interfaces may include any type of wired or wireless interface, including a Bluetooth™ interface, wireless Ethernet interface, wired Ethernet interface, USB interface, etc. Optional removable data storage can also be included. Executable logic can be stored on removable data storage media or on non-removable storage associated with the processor. The apparatus can be programmed by stored logic code in removable or internal data storage that can be introduced via one of the interfaces. The suck pressure sensor is a digital or analog pressure sensor that measures suction force in the outlet portion and reports this force for data collection and analysis; according to specific embodiments it can also report suction force to the controller to modulate or control valve operation. A number of different suitable pressure sensors are commercially available and any of those or a proprietary sensor can be used.

Embodiment in Programmed Information Appliances

Figure 11A:
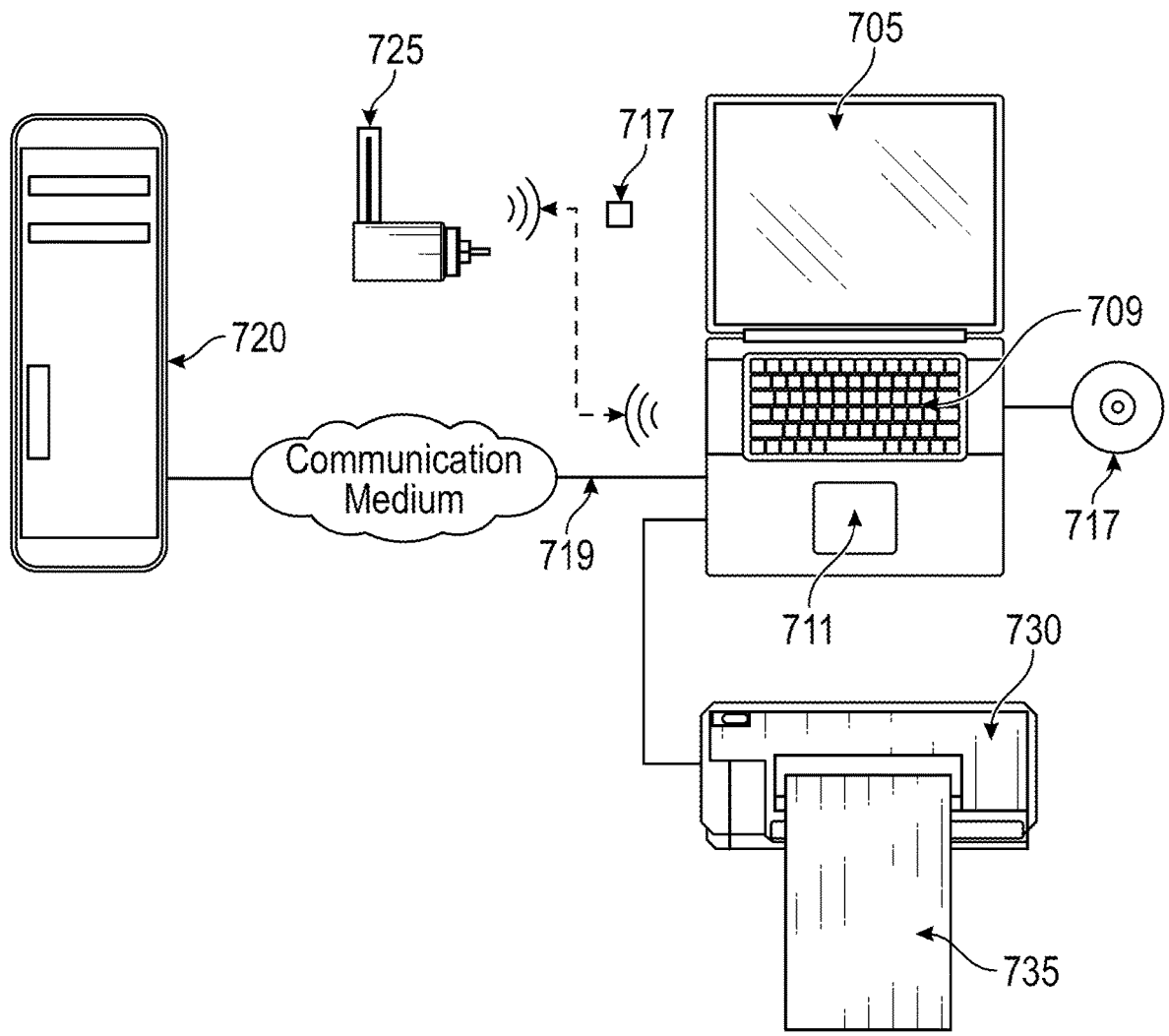
FIGS. 11A and 11B are block diagrams showing two representative example logic devices in which various aspects of the present invention may be embodied.
Figure 11B:
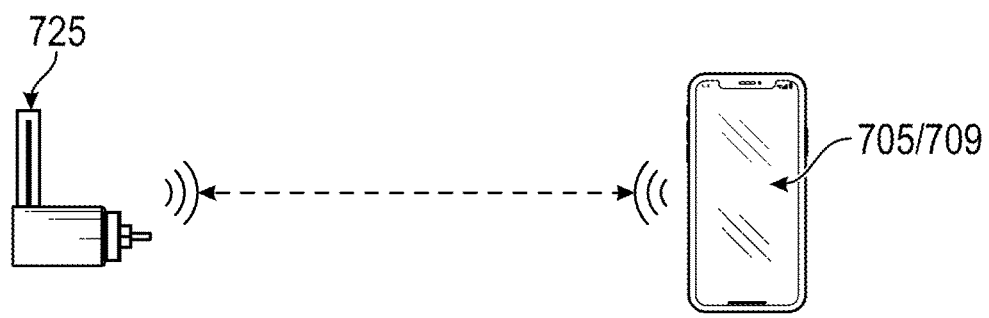

All of the methods described herein can be incorporated or programmed into Programmed Information Appliances. FIGS. 11A and 11B are block diagrams showing two representative example logic devices in which various aspects of the present invention may be embodied. As will be understood by practitioners in the art from the teachings provided herein, specific embodiments can be implemented in hardware and/or software. In some embodiments, different aspects can be implemented in either client-side logic or server-side logic. As will be understood in the art, the invention or components thereof may be embodied in a program component containing logic instructions and/or data configured on a tangible media that when loaded into an appropriately configured computing device cause that device to perform according to specific instructions. As will be understood in the art, a tangible media containing logic instructions may be preinstalled, or delivered to a user on a fixed media for physically loading into a user's computer, or the logic instructions may reside on a tangible media accessed through a remote server via a communication medium in order to download a program component.

FIGS. 11A and 11B show two different information appliances (or digital devices). Each information appliance may be understood as a logical apparatus that can read collected data or instructions, for example from media 717 and/or network port 719, which can optionally be connected to server 720 having both fixed and removable media within. Each information appliance can thereafter use those instructions to direct server or client logic. One type of logical apparatus that may embody the invention is an Orometer 725 communicating with a computer system as illustrated in FIG. 11A, containing a CPU, optional input devices 709 and 711, an appropriate drive to read external media (shown here as a CD which could be read by the correct optical drive) and optional monitor 705. Fixed media 717, or instructions delivered over port 719, may be used to program such a system and represent a broad range of devices and techniques for the storage and transfer of information, including without limitation a disk-type optical or magnetic media, magnetic tape, solid state dynamic or static memory, printer 730, shown printing graphical output 735 from the Orometer 725, etc. In specific embodiments, the invention may be embodied in whole or in part as software recorded on such media. Communication port 719 may also be used to initially receive instructions that are used to program such a system and may represent any type of communication connection. FIG. 11B demonstrates that the features described above can be miniaturized and adapted to existing commercially available devices. The example shown in FIG. 8B represents (without limitation) an Orometer 725 wirelessly transferring feeding data to an iPhone™ with monitor 705 and additional input device 709 (shown in FIG. 11B as a touchscreen). As known to developers skilled in the art, appropriate software ("apps") can easily be developed to collect, display, and process data as described herein for a wide range of different commercially available devices including, without limitation, iPhone, tablets of all types, Androids-based smartphones, and many other devices.

Specific embodiments also may be embodied in whole or in part within the circuitry of an application specific integrated circuit (ASIC) or a programmable logic device (PLD). In such a case, instructions may be embodied in a computer-understandable descriptor language, which may be used to create an ASIC, or PLD that when installed in an apparatus as herein described enables the apparatus to operate as herein described.

The invention may be embodied as an apparatus or device (e.g., a processor and a digital memory) or system for collecting and storing data as described herein and for performing the analysis and output as described herein. An apparatus or system according to specific embodiments can include logic that responds to user input to operate as herein described. Specific embodiments provide methods and/or systems that can be implemented on a general purpose or special purpose information handling appliance or logic enabled system, such as a laboratory or diagnostic or production system. The programs may be written in any suitable programming language such as C, C++, Objective-C™, Python™, Java™, assembly, or Brew™. Any suitable data or formatting specifications, such as HTML, MEL, dHTML, TIFF, JPEG, tab-delimited text, binary, etc., may be used to store data. The programs may be resident on a storage medium, e.g., magnetic or optical, e.g., the computer hard drive, a removable disk or media such as a memory stick or SD media, wired or wireless network based or Bluetooth™ based Network Attached Storage (NAS), or other removable medium. The programs may also be run over a network, for example, with a server or other machine sending signals to the local machine, which allows the local machine to carry out the operations described herein.

In the interest of clarity, not all features of an actual implementation are described in this specification. It will be understood that in the development of any such actual implementation (as in any software development project), numerous implementation-specific decisions must be made to achieve the developers' specific goals and sub-goals, such as compliance with system-related, regulatory, and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

The computers described herein may be any kind of computer, either general purpose, or special purpose computers, such as a workstation or laboratory or medical equipment. The computer may also be a handheld computer, such as a PDA, wristwatch- or eyewear-based device, tablet/pad computer, mobile phone or smart phone, or laptop, or any computing device embedded in the Orometer itself It is well known in the art that logic systems and methods such as described herein can include a variety of different components and different functions in a modular fashion. Different specific embodiments and implementations can include, for example, different mixtures of elements and functions and may group various functions as parts of various elements. For purposes of clarity, embodiments of the invention are described in terms of systems that include many different innovative components and innovative combinations of innovative components and known components. No inference should be taken to limit the claimed invention to combinations containing all of the innovative components listed in any illustrative embodiment in this specification.

Data Collection and Analysis in Example Systems

In further embodiments, an apparatus as described above is used in conjunction with software to read data from the apparatus and identify sucks in the data, outputting a list of sucks (including amplitudes and times) for analysis, either in real-time data or stored data. Sucks can be identified using pressure and time criteria, and evaluated using a wide variety of preset parameters, screening criteria, tags, mathematical formulas and/or software algorithms.

In an example of data analysis methodology, continuous records are available for each session. These give voltages from the device with oversampled data (typically at sampling rates ranging from 100-1000 Hz), which include all possible frequencies of interest. These records allow determination of the time and amplitude (pressure) of each compression and each suck in every session, which in turn allows determination of individual and cumulative $_{[SB12]}$ sucking strengths, sucks per suck burst, frequency of sucking, duration of sucking bursts and interburst pauses, over disjoint time periods by repeated measures analysis of variance at different ages. The system can also measure variability or irregularity in sucking patterns, both in suck amplitudes and in suck intervals, as given by coefficients of variation or other measures. It is also possible to examine the shapes of each suck waveform (as plotted as voltage as a function of time) to see if the shapes (e.g., bimodal or unimodal) of these waveforms are significant. In our examples, suck burst duration is measured from the peak pressure amplitude of the first suck to the last suck in the burst. Mean suck frequency is typically computed for each burst. (According to specific embodiments for each parameter, means are computed for the entire data set by computing a burst duration-weighted average of the value of the parameter for each burst.) Suck intervals are typically measured peak-to-peak.

Classification and Prediction Using Artificial Intelligence and Machine Learning Techniques The application of Artificial Intelligence (AI) and Machine Learning (ML) techniques to Orometer data can accelerate data analysis and partially automate Orometer software development. AI/ML in combination with Orometry™ can be used to help recognize different feeding behaviors, feeding states, and feeding conditions in patients, and to recognize markers associated with abnormal anatomical, physiological, craniofacial, neurodevelopmental, and neurological states; as well as other abnormal states or pathologies. This applies to any sort of feeding-monitor data, not simply to data collected by an Orometer™ as described herein.

The combination(s) of Artificial Intelligence/Machine-Learning techniques that can be used in conjunction with Orometry and other methods for monitoring and assessing feeding include, without limitation, prediction algorithms which produce synergistic predictive results when combined with feeding monitor data; and classification algorithms which produce synergistic classification results when combined with feeding monitor data. Both categories of algorithms may improve the performance of all types of feeding monitors, and thereby assist clinicians to improve screening, diagnosis, treatment and clinical care.

A large number of variables may be processed at once using AI/ML algorithms; we have routinely analyzed feeding monitor sessions with about 40 variables simultaneously during AI/ML reduction-to-practice (see Table 1). However, it can be difficult to visualize the results of AI-assisted analysis while using so many variables. We have found that in certain situations, it may be preferable to reduce the number of variables displayed at once to enhance data display.

Any known machine learning algorithm or AI algorithm may be combined with feeding monitor data to determine a classification or prediction model. The following known algorithms were used on experimental data sets, and each provided models with predictive abilities:

the "Boosted Trees" algorithm the Decision Tree algorithm the K-Nearest Neighbors (KNN) algorithm the Linear Discriminant Analysis (LDA) algorithm and the "Random Forest" algorithm.

In specific embodiments, analysis is used with the data as described herein to determine whether a subject falls within healthy parameters with regards to suck or feeding. According to specific embodiments, one or more statistical learning or machine learning (ML) classification algorithms are used to determine normal vs. nonnormal ranges. These algorithms are applied to find patterns in data sets to distinguish between subjects.

The ML (machine learning) algorithms are applied to the data to predict normal/nonnormal by creating training and testing subsets of the data using known healthy subjects and subjects with feeding abnormalities. The models are fitted to the training subset and tested on the testing subset.

Figure 12A:
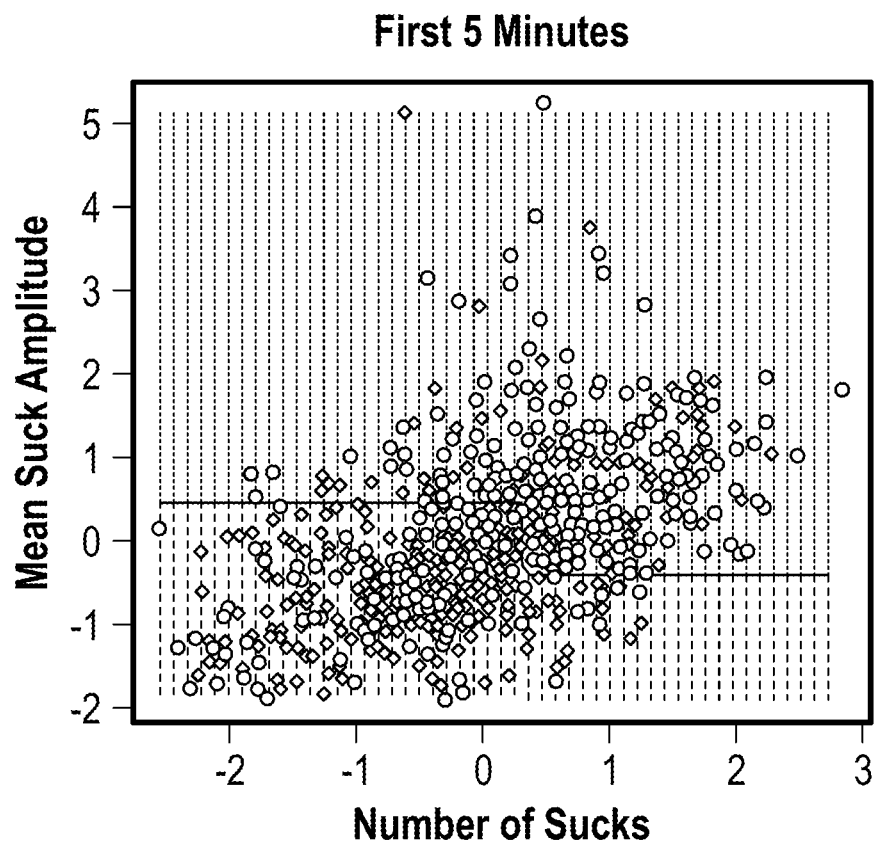
FIG. 12A illustrates a Scatterplot produced by Decision Tree algorithm distinguishing between normal and nonnormal suck patterns from very small dataset according to specific embodiments.
Figure 12B:
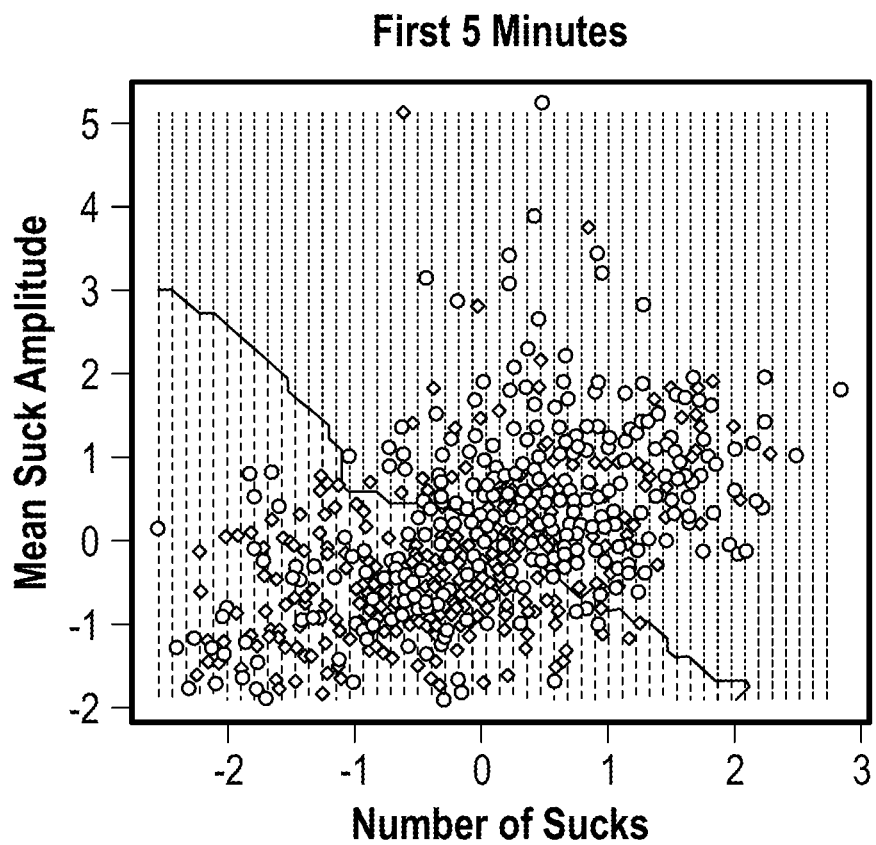
FIG. 12B illustrates a Scatterplot produced by KNN algorithm distinguishing between normal and nonnormal suck patterns from very small dataset according to specific embodiments.

According to further embodiments, only a subset of the most important variables are used to determine normal vs. non-normal subjects, such as: integrated area, suck amplitude, number of sucks, or fraction of time with activity. Running these algorithms on these variables taken two at a time may, under certain circumstances, produce results with similar accuracy as when all of the variables are run simultaneously. However, additional advantages are gained in data display, including, without limitation, the ability to draw scatter plots and decision regions (critical regions) which reveal how the algorithms are working. We can see how the decisions or predictions are made, and we can see how much can be expected in general from these kinds of algorithms. FIGS. 12A-12B show scatterplots produced from a very small dataset of 366 normal subjects and 311 nonnormal subjects using three of the AI/ML algorithms tested in a preliminary trial. Despite the fact that the dataset tested was approximately 1000 times smaller than datasets used in typical AI/ML applications, all three algorithms showed clear ability to distinguish between normal and nonnormal subjects on a statistical basis. One of the algorithms tested, Random Forest (no Figure), showed a sensitivity of 74% and a specificity of 61%, even when working from a miniscule dataset (by typical ML standards).

In one example according to specific embodiments, the variables shown in Table 1 are used. The subjects in this example were indicated as normal or nonnormal. We search the diagnostic category for subjects labeled 'normal', and create a categorical variable based on this, with two categories: 'normal' and 'nonnormal'. In a specific experiment, each variable was scaled by subtracting its mean and dividing by its standard deviation so that ML algorithms do not have a bias in favor of variables with larger values.

TABLE 1

| | | | | | | |
|---|---|---|---|---|---|---|
| 1 | $ n_sucks | 0.145 | 1.065 | 2.017 | −0.687 | −1.108 |
| 2 | $ suck_amp_mean | 0.8094 | 0.4458 | 0.0432 | −0.3111 | 0.6671 |
| 3 | $ suck_amp_median | 0.756 | 0.318 | 0.108 | −0.332 | 0.407 |
| 4 | $ suck_amp_q1 | 0.523 | 0.347 | 0.143 | −0.638 | −0.198 |
| 5 | $ suck_amp_q1.1 | 0.9121 | 0.4621 | 0.2686 | −0.0726 | 1.1524 |

TABLE 1-continued

| | | | | | | |
|---|---|---|---|---|---|---|
| 6 | $ n_sucks_small | −0.784 | −0.665 | −1.022 | 0.642 | −0.606 |
| 7 | $ suck_area_mean | 1.166 | 0.537 | 1.892 | −0.014 | 1.241 |
| 8 | $ suck_uptake_slope | −0.515 | −0.166 | −0.971 | −0.527 | 0.325 |
| 9 | $ suck_freq | −1.012 | −0.183 | −2.022 | −1.868 | −1.349 |
| 10 | $ suck_int | 0.725 | −0.118 | 2.066 | 1.918 | 1.089 |
| 11 | $ suck_amp_var | −0.0725 | −0.5099 | −0.4949 | 0.7098 | 2.1758 |
| 12 | $ suck_amp_cv | −0.327 | 0.0942 | −0.3311 | 0.6572 | 0.5696 |
| 13 | $ suck_int_cv | 0.461 | 0.134 | −1.361 | 0.435 | 1.005 |
| 14 | $ n_bursts | −0.0546 | −1.4419 | −1.0951 | −0.0546 | −0.7483 |
| 15 | $ sucks_per_burst | −0.358 | 3.298 | −0.483 | −0.446 | −0.387 |
| 16 | $ burst_dur_mean | −0.298 | 3.815 | −0.406 | −0.364 | −0.315 |
| 17 | $ burst_dur_max | 0.192 | 2.89 | −0.584 | −0.549 | −0.611 |
| 18 | $ burst_dur_cv | 0.6083 | −3.1019 | 0.2399 | −0.0029 | −0.8257 |
| 19 | $ pause_dur_mean | −0.488 | −1.574 | −0.502 | 0.441 | 1.273 |
| 20 | $ pause_dur_max | −0.52 | −0.979 | −0.616 | 0.147 | 1.325 |
| 21 | $ pause_dur_cv | −0.0425 | −2.0628 | 0.0871 | 0.3317 | 1.6023 |
| 22 | $ activity_amp_mean | 0.669 | 0.481 | 0.715 | −0.391 | 0.851 |
| 23 | $ activity_fraction_time | 0.852 | 1.39 | −1.911 | −0.195 | −0.922 |
| 24 | $ n_sucks_fourier | 0.181 | 1.133 | −1.946 | −0.754 | −1.329 |
| 25 | $ activity_freq_fourier | −0.918 | −0.176 | −2.065 | −1.244 | −1.674 |
| 26 | $ irreg_mean | −0.5009 | 0.0869 | −0.8264 | 0.7842 | 0.3349 |
| 27 | $ irreg_med | −0.551 | 0.175 | −1.023 | 0.882 | 0.295 |
| 28 | $ act._frac_of_T_regular | 0.915 | 0.63 | −0.737 | −0.587 | −0.677 |
| 29 | $ act._frac._of_activity_regular | 0.6613 | 0.0319 | 1.3645 | −0.6273 | −0.2756 |
| 30 | $ n_activity_bursts | −0.2482 | −1.3936 | −1.0664 | 0.0791 | −0.9027 |
| 31 | $ activity_burst_dur_mean | −0.249 | 3.82 | −0.405 | −0.39 | −0.209 |
| 32 | $ activity_burst_dur_max | −0.421 | 3.022 | −0.579 | −0.537 | −0.358 |
| 33 | $ activity_burst_dur_cv | −0.338 | −2.933 | 0.285 | 0.279 | −0.468 |
| 34 | $ activity_pause_dur_mean | −0.515 | −1.538 | −0.398 | 0.271 | 1.882 |
| 35 | $ activity_pause_dur_max | −0.679 | −0.994 | −0.634 | 0.174 | 1.252 |
| 36 | $ activity_pause_dur_cv | −0.335 | −2.078 | −0.194 | 0.49 | 1.362 |
| 37 | $ integrated_area | 0.842 | 0.985 | −0.892 | −0.436 | −0.178 |
| 38 | $ n_short_bursts | −0.396 | −0.717 | −0.717 | 0.246 | −0.717 |
| 39 | $ n_singleton_bursts | −0.55 | −0.55 | −0.55 | 0.258 | −0.55 |

In a second example, we discard all variables except suck amp mean and n sucks (mean suck amplitude, and number of sucks). This allows production of scatterplots similar to the ones shown in FIGS. 12A-12B.

Conclusion

The general structure and techniques, and more specific embodiments that can be used to effect different ways of carrying out the more general goals are described herein. Although only a few embodiments have been disclosed in detail herein, other embodiments are possible and the inventor(s) intend these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art.

The inventors intend that only those claims which use the words "means for" are intended to be interpreted under 35 U.S.C. § 112$_{[SB13]}$, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

All references, publications, patents, and patent applications cited herein are hereby incorporated by reference in their entirety for all purposes.

REFERENCES

U.S. Pat. No. 6,109,100
U.S. Pat. No. 8,473,219 (issued Jun. 25, 2013 to Kaplan, Medoff-Cooper, et al.).
U.S. Pat. No. 8,413,502 (issued Apr. 9, 2013 to Zemel, Medoff-Cooper et al.)
[SB16] Lang W C, Buist N R M, Geary A, Buckley S, Adams E, Jones A J, Gorsek S, Winter S C, M D, Tran H, Rogers B R. Quantification of Intraoral Pressures during Nutritive Sucking: Methods with Normal Infants. *Dysphagia*, 19 Sep. 2010.

What is claimed:

1. A method of measuring or characterizing feeding activity comprising (nutritive sucking) using a computing device having a processor and a memory, the method comprising:
the processor accessing digital data derived from one or more monitoring instruments indicating the feeding activity during a period of time;
the processor determining a suck-pressure baseline for the digital data;
the processor employing a two-pass suck-recognition strategy comprising a first pass identifying sucks comprising relatively larger deflections in the digital data relative to the suck-pressure baseline, and a second pass identifying further sucks comprising relatively smaller deflections relative to the suck-pressure baseline that are not superimposed on the relatively larger deflections;
the processor determining features of the digital data relating to the feeding activity based on the identified sucks and identified further sucks from the employing the two-pass suck-recognition strategy, including one or more of:

measures related to sucking comprising suck amplitude, suck frequency, or consistency of sucking;

measures related to suck bursts comprising duration or suck-burst pauses;

measures comprising use of Fourier transform to infer suck frequency and number of sucks without relying upon identification of individual sucks or bursts of sucks;

ratio of active feeding time to pauses;

the processor determining consistency and strength of feeding based on the features; and the processor reporting consistency and strength of feeding or quantitative values for the features.

2. The method of claim 1 wherein the processor accesses digital data during data collection and determines features of the data in real time.

3. The method of claim 1 further comprising:

analyzing monitoring data from the one or more monitoring instruments immediately at time of collection to determine real-time values or signals that accurately correspond to or characterize feeding or drinking activity.

4. The method of claim 1 wherein the digital data comprises measurements indicating pressure over time.

5. The method of claim 1 wherein the determining the suck-pressure baseline comprises determining a data curve that represents a neutral pressure.

6. The method of claim 1 wherein the determining the suck-pressure baseline comprises computing a running minimum or maximum curve and then smoothing the running minimum or maximum curve it.

7. The method of claim 1 wherein the determination of the suck-pressure baseline comprises correcting for baseline wander or offset, and determining a proxy baseline for neutral pressure that will follow a part of the suck which would correspond to zero pressure if baseline wander or offset were not present.

8. The method of claim 1 further comprising:

the processor identifying events of the data relating to feeding activity, such as nutritive sucks and suck bursts.

9. The method of claim 8 wherein the identifying events comprises identification of individual nutritive sucks and suck bursts.

10. The method of claim 8 wherein the identifying events comprises performing a running average of the digital data to derive a smooth data curve where feeding actions comprising sucks are identified as deflections comprising local minima or maxima of sufficient amplitude of the smoothed curve measured against the suck-pressure baseline.

11. The method of claim 10 wherein a smoothing process used to derive the smooth data curve is tuned to avoid identifying bimodal or bifurcated shapes.

12. The method of claim 10 wherein a smoothing process used to derive the smooth data curve is tuned to avoid identifying as separate sucks bimodal or bifurcated shapes found in one or more deflections.

13. The method of claim 10 wherein a smoothing process used to derive the smooth data curve uses the second pass with the smoothing process tuned to produce the smoothed curve that follows the deflections more closely.

14. The method of claim 8 wherein the identifying events is applicable to characterize the strength and consistency of infant feeding and comprises:

(1) smoothing the digital data to determine a smoothed data signal;

(2) scanning for zero-crossings of a derivative of the smoothed data signal; and (3) using the two-pass suck-recognition strategy comprising:

(a) first identifying the relatively larger deflections, and (b) then identifying the relatively smaller deflections that are not superimposed upon the larger deflections.

15. The method of claim 14 wherein the second pass, comprising (3)(b) of the two-pass suck-recognition strategy, finds relatively smaller deflections that if within bounds of an already-found relatively larger deflection, are ignored and the already-found relatively larger deflection is determined to be feeding action comprising a suck.

16. The method of claim 14 wherein the second pass, comprising (3)(b) of the two-pass suck-recognition strategy, identifies missed relatively small deflections.

17. The method of claim 8 wherein the identifying events comprises determining suck bursts from suck intervals comprising time duration from one event comprising a suck peak to a next event comprising a next suck peak.

18. The method of claim 17 wherein sucks are grouped into bursts when a suck interval is greater than a predetermined minimum value in a range of 1 to 8 seconds.

19. The method of claim 8 wherein the identifying events comprises determining an area under a tracing indicating a fraction of time showing activity for use as a proxy for suck burst values.

20. The method of claim 19 wherein the fraction of time showing activity is computed by cutting the time interval under analysis into subintervals and determining what fraction of the subintervals show an integrated area of a pre-set value comprising a value of pressure and time.

21. The method of claim 19 wherein the determined area under the tracing is computed by integrating between the tracing and the suck-pressure baseline curve.

22. The method of claim 19 wherein the determined area under the tracing is a proxy for amplitude and area of sucks, and does not depend upon identification of sucks.

23. The method of claim 19 wherein the determined area under the tracing correlates t the volume consumed through the feeding activity.

24. The method of claim 8 wherein the identifying events comprises using Fourier analysis to measure frequency of sucking.

25. The method of claim 1 wherein the determining features comprises determining values for average suck rate and suck burst using proxy measures based on Fourier transforms of the data that do not require identification of individual sucks or bursts.

26. The method of claim 1 wherein the determining comprises using a dominant Fourier transform frequency of the digital data to determine suck count without identification of individual sucks.

27. The method of claim 1 further comprising:

characterizing infant feeding behavior during an interval as regular and consistent feeding behavior; chaotic, irregular, or inconsistent feeding behavior; or undetermined feeding behavior.

28. The method of claim 27 further wherein the characterizing comprises determining a value for variability of suck amplitudes during a suck burst, variability of spacing between sucks in a suck burst or both.

29. The method of claim 27 further wherein the characterizing comprises using non-suck-based measures of a concentration of a Fourier transform about a primary frequency of feeding where a relatively high concentration of the Fourier transform indicates a strongly rhythmic feeding pattern and a relatively low concentration of the Fourier transform indicates a more chaotic feeding pattern.

30. The method of claim 27 further wherein the characterizing comprises determining a coefficient of variation of suck amplitudes or of suck intervals by determining a standard deviation of these values divided by their mean.

31. The method of claim 27 further wherein the characterizing comprises determining suck amplitude variability by computing a standard deviation of ratios of amplitudes of consecutive sucks.

32. The method of claim 27 further wherein the characterizing comprises determining scatterplots demonstrating suck-to-suck changes in amplitude by plotting each suck with the amplitude of the following suck.

33. The method of claim 27 further wherein the characterizing comprises determining histograms of percent changes in suck amplitudes or suck intervals from suck to suck.

34. The method of claim 1 wherein the determining features comprises one or more of: proxy measures of feeding persistence or number and duration of bursts;
    proxy measures comprising using a fraction of time showing feeding behavior;
    measuring an area underneath determined sucks during a particular time interval comprising an integrated area of sucking which correlates with volume consumed; and
    determining values for number of bursts and burst durations as an indication of halting or fatigue in feeding.

35. The method of claim 1 further comprising:
    the processor accessing one or more machine learning trained models and comparing data to trained models to determine if the data indicates normal or non-normal feeding or sucking.

36. The method of claim 35 further comprising:
    comparing data to trained models in near real time to provide a real time indication of normal or non-normal feeding or sucking.

37. The method of claim 1, further for classification of feeding-monitor data or sucking monitor data, comprising:
    accessing a model from one or more classification or prediction models determined from a data set of classified feeding-monitor data or sucking monitor data that has been classified into at least two different classifications using a machine learning algorithm or artificial intelligence (AI) algorithm;
    collecting further feeding-monitor data or sucking monitor data from a subject; and
    using the processor and the model to determine if said collected further feeding-monitor data or sucking monitor data is in a first classification or a second classification.

38. The method of claim 37 further comprising storing the model for later use in classification.

39. The method of claim 37 further comprising using one or more of the following algorithms on experimental data sets to determine models with predictive abilities:
    "Boosted Trees" algorithm;
    Decision Tree algorithm;
    K-Nearest Neighbors (KNN) algorithm;
    Linear Discriminant Analysis (LDA) algorithm; and
    "Random Forest" algorithm.

40. The method of claim 37 further comprising:
    using one or more of the one or more classification or prediction models to recognize different feeding behaviors and/or feeding states and/or feeding conditions in subjects or patients for collected data.

41. The method of claim 37 further comprising:
    using one or more of the one or more classification or prediction models to recognize from collected data markers associated with one or more of: abnormal anatomical, physiological, craniofacial, neurodevelopmental, neurological states; or other abnormal states or pathologies.

42. The method of claim 37 further wherein the method is used in conjunction with an automated feeding monitor.

43. The method of claim 37 further wherein the method is used in conjunction with data collected by a feeding-monitor.

44. The method of claim 37 further comprising:
    the processor using real time data collection and predictive models to generate synergistic predictive results when combined with feeding monitor data; and
    the processor using classification algorithms which produce synergistic classification results when combined with feeding monitor data.

45. The method of claim 37 further comprising using greater than 10 different feeding or sucking monitor variables to determine predictive models.

46. The method of claim 37 further comprising using greater than 20 different feeding or sucking monitor variables to determine predictive models.

47. The method of claim 37 further comprising using greater than 30 different feeding or sucking monitor variables to determine predictive models.

48. The method of claim 37 further comprising using two or more different feeding or sucking monitor variables to determine predictive models.

49. The method of claim 37 further comprising: determining whether a subject has one or more feeding abnormalities, with regards to suck or feeding.

50. The method of claim 37 further comprising:
    applying machine learning or AI algorithms to the digital data or further processed data therefrom to predict healthy feeding or feeding abnormality by creating, training and testing subsets of the digital data or further processed data therefrom using known normal and non-normal subjects, fitting models to the training subsets, and testing the models on the testing subsets of the digital data or further processed data therefrom.

51. The method of claim 37 further wherein:
    a subset of variables is used to determine normal vs. non-normal subjects with regard to feeding abnormality, the subset consisting of one or more of: integrated area, suck amplitude, number of sucks, or fraction of time with activity.

52. The method of claim 37, wherein the method is performed by the computing device having the processor and the memory operable as a computing system for model training and data classification.

53. A fully automated system for measuring or characterizing activity comprising nutritive sucking, comprising:
    a computing device having a processor and a memory;
    the computing device arranged to access digital data derived from one or more monitoring instruments indicating the feeding activity during a period of time;
    the processor arranged to determine a suck-pressure baseline for the digital data;
    the processor arranged to employ a two-pass suck-recognition strategy comprising a first pass identifying sucks comprising relatively larger deflections in the digital data relative to the suck-pressure baseline, and a second pass identifying further sucks comprising relatively smaller deflections relative to the suck-pressure baseline that are not superimposed on the relatively larger deflections;

the processor arranged to determine features of the digital data relating to the feeding activity based on the identified sucks and identified further sucks from the employing the two-pass suck-recognition strategy, including one or more of:

measures related to sucking comprising suck amplitude, suck frequency, or consistency of sucking;

measures related to suck bursts comprising duration or suck-burst pauses;

measures comprising use of Fourier transform to infer suck frequency and number of sucks without relying upon identification of individual sucks or bursts of sucks;

ratio of active feeding time to pauses;

the processor arranged to determine consistency and strength of feeding based on the determined features of the digital data relating to the feeding activity; and the processor arranged to report consistency and strength of feeding or quantitative values for the determined features of the digital data relating to the feeding activity.

54. A tangible, non-transitory, computer-readable media having instructions thereupon which, when executed by a processor, cause the processor to perform a method for measuring or characterizing activity comprising nutritive sucking comprising:

the processor accessing digital data derived from one or more monitoring instruments indicating the feeding activity during a period of time;

the processor determining a suck-pressure baseline for the digital data;

the processor employing a two-pass suck-recognition strategy comprising a first pass identifying sucks comprising relatively larger deflections in the digital data relative to the suck-pressure baseline, and a second pass identifying further sucks comprising relatively smaller deflections relative to the suck-pressure baseline that are not superimposed on the relatively larger deflections;

the processor determining features of the digital data relating to the feeding activity based on the identified sucks and identified further sucks from the employing the two-pass suck-recognition strategy, including one or more of:

measures related to sucking comprising suck amplitude, suck frequency, or consistency of sucking;

measures related to suck bursts comprising duration or suck-burst pauses;

measures comprising use of Fourier transform to infer suck frequency and number of sucks without relying upon identification of individual sucks or bursts of sucks;

ratio of active feeding time to pauses;

the processor determining consistency and strength of feeding based on the determined features of the digital data relating to the feeding activity; and the processor reporting consistency and strength of feeding or quantitative values for the determined features of the digital data relating to the feeding activity.

55. The tangible, non-transitory, computer-readable media of claim 54 wherein the determination of the suck-pressure baseline comprises correcting for baseline wander or offset, and determining a proxy baseline for neutral pressure that will follow a part of the suck which would correspond to zero pressure if baseline wander or offset were not present.

* * * * *